United States Patent
Naccarato et al.

(10) Patent No.: US 12,369,608 B2
(45) Date of Patent: *Jul. 29, 2025

(54) HIGH FIBER, HIGH PROTEIN, LOW CARBOHYDRATE FLOUR, SWEETENED LIQUID, SWEETENERS, CEREALS, AND METHODS FOR PRODUCTION THEREOF

(71) Applicant: AGRIFORCE GROWING SYSTEMS LTD., Vancouver (CA)

(72) Inventors: David Clayton Naccarato, Kingston, ID (US); Stuart Gray Gordon, Dillon, CO (US)

(73) Assignee: AGRIFORCE GROWING SYSTEMS LTD., Vancouver (CA)

( * ) Notice: Subject to any disclaimer, the term of this patent is extended or adjusted under 35 U.S.C. 154(b) by 153 days.

This patent is subject to a terminal disclaimer.

(21) Appl. No.: 17/963,690

(22) Filed: Oct. 11, 2022

(65) Prior Publication Data
US 2023/0031973 A1    Feb. 2, 2023

Related U.S. Application Data

(63) Continuation of application No. 15/885,118, filed on Jan. 31, 2018, now Pat. No. 11,540,538.
(Continued)

(51) Int. Cl.
*A23L 7/104*      (2016.01)
*A21D 2/38*       (2006.01)
(Continued)

(52) U.S. Cl.
CPC .............. *A23L 7/104* (2016.08); *A21D 2/38* (2013.01); *A23L 7/198* (2016.08); *A23L 7/25* (2016.08);
(Continued)

(58) Field of Classification Search
CPC . A23L 7/104; A23L 7/198; A23L 7/25; A23L 11/20; A23L 19/15; A23L 11/09;
(Continued)

(56) References Cited

U.S. PATENT DOCUMENTS 3,958,015 A    5/1976  Gay
4,828,846 A    5/1989  Rasco
(Continued)

FOREIGN PATENT DOCUMENTS

GB    1025263 A  *  4/1966  ............. C12C 1/047
WO    2006/119217 A3    11/2006
(Continued)

OTHER PUBLICATIONS

Briggs, "Brewing Science and Practices", Woodhead Publishing Ltd., 2004, pp. 1-245 (Year: 2004).*
(Continued)

*Primary Examiner* — Changqing Li
(74) *Attorney, Agent, or Firm* — Norton Rose Fulbright Canada LLP

(57) ABSTRACT

A technique for processing ancient, heritage and modern wheat, grains, seeds, beans, legumes, tuber and root vegetables create baking flours suitable for human consumption. The initial ingredient is incubated to initiate germination and activate internal enzymes and nutrient production for useful enzymes, proteins and nutrients. Germination is terminated and the product wet-milled to fracture or shear the outer hull, exposing the inner grain. The product is mixed with water at varying temperatures during which amylase is added. The mixture is incubated to facilitate saccharification of starches into sugars by the amylase enzymes. The mixture is pasteurized to denature the amylases and the mash pressed and/or strained to separate the liquid and solids. The solid phase is dried and milled into higher fiber, high protein, low
(Continued)

*A List of Substrates that may be used in the Inventive Flour process*

NOTE: The following is a general category list of each item. In ALL cases these include all varieties and versions of these type of grains, legumes and root vegetables. For example "rice" includes all varieties including non-glutinous and glutinous varieties. This list will also include all ancient, heritage, wild and modern grains, seeds, beans and legumes.

| Grains | Grains | Legumes | Tubers and Root Vegetable |
|---|---|---|---|
| Wheat* | Sorghum | Beans** | Beets |
| Barley | Amaranth | Lentils | Carrots |
| Rye | Trtitcale | Peas | Taro |
| Oats | Flax | Peanuts | Yams |
| Buckwheat | Teff | Lupins | Sweet Potatoes |
| Rice | Millet (Ferrio) | | Turnips |
| Wild Rice | Kasha | | Rutabagas |
| Couscous | Quinoa | | |
| Corn | Kernza | | |

* All varieties of wheat which includes but not limited to the following: Soft White Winter Wheat, Hard Red Winter Wheat, Hard Red Spring Wheat, Soft Red Winter Wheat, Soft White Spring Wheat, Duram Wheat, Khorasan (Kamut), Einkorn, Spelt (Dinkel Wheat), Farro, and Bulgar.
** Beans include all varieties carbohydrate flour. The liquid is carbohydrate-rich with substantial fiber, protein and other nutrients dissolved in the solution.

17 Claims, 8 Drawing Sheets

Related U.S. Application Data

(60) Provisional application No. 62/453,308, filed on Feb. 1, 2017.

(51) Int. Cl.

| | | |
|---|---|---|
| *A23L 7/10* | (2016.01) | |
| *A23L 7/25* | (2016.01) | |
| *A23L 11/50* | (2021.01) | |
| *A23L 11/70* | (2021.01) | |
| *A23L 19/10* | (2016.01) | |
| *A23L 19/15* | (2016.01) | |
| *A23L 27/10* | (2016.01) | |
| *A23L 33/10* | (2016.01) | |
| *C12P 19/12* | (2006.01) | |
| *C12P 19/14* | (2006.01) | |
| *C12P 19/22* | (2006.01) | |

(52) U.S. Cl.
  CPC .............. *A23L 11/50* (2021.01); *A23L 11/70* (2021.01); *A23L 19/10* (2016.08); *A23L 19/15* (2016.08); *A23L 27/10* (2016.08); *A23L 33/10* (2016.08); *C12P 19/12* (2013.01); *C12P 19/14* (2013.01); *C12P 19/22* (2013.01); *C12Y 302/01001* (2013.01); *A23V 2002/00* (2013.01)

(58) Field of Classification Search
  CPC .......... A23L 27/10; A23L 19/10; C12P 19/14; C12P 19/22
  See application file for complete search history.

(56) References Cited

U.S. PATENT DOCUMENTS

| | | | |
|---|---|---|---|
| 4,857,339 | A | 8/1989 | Maselli |
| 11,540,538 | B2 * | 1/2023 | Naccarato ............... A23L 27/10 |
| 2005/0129823 | A1 | 6/2005 | Dohl |
| 2006/0160189 | A1 | 7/2006 | Hammond |
| 2008/0317725 | A1 * | 12/2008 | Baum .................. A61K 31/122 |
| | | | 424/463 |
| 2009/0031458 | A1 * | 1/2009 | Stahl .................. C12N 15/8242 |
| | | | 536/23.6 |
| 2010/0278970 | A1 | 11/2010 | Duan |
| 2011/0177199 | A1 | 7/2011 | Harvey |
| 2012/0309038 | A1 * | 12/2012 | Moser ...................... C12Q 1/40 |
| | | | 435/22 |
| 2013/0183404 | A1 | 7/2013 | Whalen |
| 2015/0152442 | A1 | 6/2015 | Ge |

FOREIGN PATENT DOCUMENTS

| | | |
|---|---|---|
| WO | 2009/074650 A2 | 6/2009 |
| WO | 2015153264 A1 | 10/2015 |

OTHER PUBLICATIONS

American Homebrewer Association, "Accidental High Mash out" [Online], published Nov. 18, 2015, [retrieved on Jan. 23, 2023]. Retrieved from the Internet: <URL: https://www.homebrewersassociation.org/forum/index.php?topic=25026.0> (Year: 2015).*

Growler, Spent, but Still of Value: Ideas for Re-using Brewing Grains [Online], published Dec. 26, 2012, [retrieved on Dec. 29, 2020]. Retrieved from the Internet: <URL: https://www.growlermag.com/spent-but-valuable-ideas-for-using-spent-grain/> (Year: 2012).*

Smith, Storing Your Beer Brewing Hops, Grain and Yeast [Online], published Feb. 8, 2014, [retrieved on Sep. 27, 2019]. Retrieved from the Internet: <URL: http://beersmith.com/blog/2014/02/08/storing-your-beer-brewing-hops-grains-and-yeast/> (Year: 2014).*

Anderson, J.W., et al., "Health benefits of Dietary Fiber," Nutrition Reviews 67(188):1-25, Mar. 25, 2009, <https://onlinelibrary.wiley.com/doi/full/10.1111/j.1753-4887.2009.00189.x>, [retrieved Jul. 13, 2018], 25 pages.

Briggs, D.E., "Malts and Malting," Springer Science & Business Media, 1998.

Ciesielski, V., et al., "Comparison of Evolutionary and Conventional Feature Extraction Methods for Malt Classification," 2012 IEEE Congress on Evolutionary Computation, Brisbane, Australia, Jun. 10-15, 2012, 7 pages.

Colditz, Graham A., et al., "Healthy Diet in Adults," UptoDate.com, Dec. 11, 2019, <http://www.uptodate.com/home>, 1 page.

Duyff, Roberta Larson, "Carbs: Sugar, Starches, Fiber," American Dietetic Association Complete Food and Nutrition Guide, 4th ed., John Wiley & Sons, Hoboken, N.J., 2012, pp. 55-87.

Fărcaş, A. C., et al., "Volatile Profile, Fatty Acids Composition and Total Phenolics Content of Brewers' Spent Grain By-Product with Potential Use in the Development of New Functional Foods," Journal of Cereal Science 64: 34-42.

Finley, J. W., et al., "Milling and Baking Properties of Dried Brewer's Spent Grain," Cereal Chemistry 57(3):166-168. 1980.

Institute of Medicine, "Dietary Reference Intakes for Energy, Carbohydrate, Fiber, Fat, Fatty Acids, Cholesterol, Protein, and Amino Acids," National Academy Press, Washington D.C., 2005, Chapter VII, "Dietary, Functional, and Total Fiber," pp. 339-421.

Johnston, R., et al., "Controlled Sprouting in Wheat Increases Quality and Consumer Acceptability of Whole-Wheat Bread," Cereal Chemistry 96(5): 866-877, 2019.

Maga, Joseph A., et al., "Chemical and Sensory Properties of Wholewheat Pasta Products Supplemented with Wheat-Derived Dried Distillers Grain (DDG)," Journal of Food Processing and Preservation 13(1): 71-78, 1989.

Magabane, I. E., "Technologies for Improving the Quality of Bread Doughs Made with Barley Spent Grain and Sorghum," master's thesis, University of Pretoria, South Africa, 2017.

"Most Popular Health News Articles for 2017," @2004-2018 Medical News Today, <https://www.medicalnewstoday.com/popular/2017>, 10 pages.

Rasco, Barbara A., et al., "Baking Properties of Breads and Cookies Incorporating Distillers' or Brewer's Grains from Wheat or Barley," Journal of Food Science 55(2):424-429, 1990.

Rasco, Barbara A., et al., "Consumer Acceptability of Baked Goods Containing Distillers' Dried Grains with Solubles from Soft White Winter Wheat," Cereal Chemistry 64(3):139-143, 1987.

Rasco, Barbara A., et al. "Iron, Calcium, Zinc and Phytic Acid Content of Yeast-Raised Breads Containing Distillers' Dried Grains and Other Fiber Ingredients," Journal of Food Composition and Analysis 3(1):88-95, 1990.

Rasco, Barbara A. et al., "Sensory Evaluation of Baked Goods Incorporating Different Levels of Distillers' Dried Grains with Solubles from White Wheat," Journal of Food Science 54(2):337-342, 1989.

Reddy, N. R., et al., "Supplementation of Wheat Muffins with Dried Distillers Grain Flour," Journal of Food Quality 9(4): 243-249, 1986.

San Buenaventura, Maria L., et al. "The Total Dietary Fiber Content of Distillers' Dried Grains with Solubles," Cereal Chemistry 64(2):135-136, 1987.

Slavin, Joanne L., "Position of the American Dietetic Association: Health Implications of Dietary Fiber," Journal of the American Dietetic Association, 108(10):1716-1731, Oct. 2008.

Tsen, C. C., et al., "Evaluation of Distillers' Dried Grain Flour as a Bread Ingredient," Cereal Chemistry 60(4):295-297, 1983.

Turner, H., et al., "Effect of Steeping Regime on Barley Malt Quality and Its Impacts on Breeding Program Selection," Journal of the American Society of Brewing Chemists 77(4): 267-281, 2019.

(56) References Cited

OTHER PUBLICATIONS

Waters, D. M., et al., "Fibre, Protein and Mineral Fortification of Wheat Bread Through Milled and Fermented Brewer's Spent Grain Enrichment," European Food Research and Technology 235(5): 767-778, 2012.

"Whole Grains and Fiber," American Heart Association, Oct. 11, 2016, <http://www.heart.org/HEARTORG/GettingHealthy/NutritionCenter/HealthyDietGoals/Whole-Grains-and-Fiber UCM 303249 Article.jsp> [retrieved Jul. 13, 2018], 2 pages.

International Search Report and Written Opinion mailed Apr. 12, 2018, in International Patent Application No. PCT/US2018/016274, filed Jan. 31, 2018, 14 pages.

Supplementary European Search Report dated Jun. 2, 2020, issued in European Patent Application No. 18747157.8. filed Jan. 31, 2018, 10 pages.

* cited by examiner

*A List of Substrates that may be used in the Inventive Flour process*

*NOTE: The following is a general category list of each item. In ALL cases these include all varieties and versions of these type of grains, legumes and root vegetables. For example "rice" includes all varieties including non-glutinous and glutinous varieties. This list will also include all ancient, heritage, wild and modern grains, seeds, beans and legumes.*

| *Grains* | *Grains* | *Legumes* | *Tubers and Root Vegetable* |
|---|---|---|---|
| Wheat* | Sorghum | Beans** | Beets |
| Barley | Amaranth | Lentils | Carrots |
| Rye | Trtitcale | Peas | Taro |
| Oats | Flax | Peanuts | Yams |
| Buckwheat | Teff | Lupins | Sweet Potatoes |
| Rice | Millet (Ferrio) | | Turnips |
| Wild Rice | Kasha | | Rutabagas |
| Couscous | Quinoa | | |
| Corn | Kernza | | |

* All varieties of wheat which includes but not limited to the following: Soft White Winter Wheat, Hard Red Winter Wheat, Hard Red Spring Wheat, Soft Red Winter Wheat, Soft White Spring Wheat, Duram Wheat, Khorasan (Kamut), Einkorn, Spelt (Dinkel Wheat), Farro, and Bulgar.
** Beans include all varieties

FIG. 1

Table

|        | Sprouted Grain | APF | Inventive Flour | % Difference Inventive Flour/APF |
|--------|----------------|-----|-----------------|----------------------------------|
| Protein| 12%            | 10% | 23%             | 230%                             |
| Fiber  | 12%            | 3%  | 46%             | 1520%                            |
| Starch | 52%            | 70% | 8%              | 9%                               |

ID
HIGH FIBER, HIGH PROTEIN, LOW CARBOHYDRATE FLOUR, SWEETENED LIQUID, SWEETENERS, CEREALS, AND METHODS FOR PRODUCTION THEREOF

CROSS REFERENCE TO RELATED APPLICATIONS

This application is a continuation of U.S. patent application Ser. No. 15/885,118, filed Jan. 31, 2018, entitled "HIGH FIBER, HIGH PROTEIN, LOW CARBOHYDRATE FLOUR, SWEETENED LIQUID, SWEETENERS, CEREALS, AND METHODS FOR PRODUCTION THEREOF," which claims the benefit of U.S. Provisional Patent Application No. 62/453,308, filed Feb. 1, 2017, entitled "HIGH FIBER, HIGH PROTEIN, LOW CARBOHYDRATE FLOUR AND POWER JUICE AND METHODS FOR PRODUCTION THEREOF," the disclosures of which are incorporated herein by reference in their entirety.

BACKGROUND OF THE INVENTION

Field of the Invention

The present disclosure related generally to food products, and, more specifically to techniques to produce high fiber, high protein, low carbohydrate flour, cereals, sweeteners and a sweetened liquid derived from various substrate products.

Description of the Related Art

Over the past two decades, many countries have become very health conscious and have tried to eliminate poor nutritional elements from the everyday diet. This includes trans-fats, high cholesterol foods, high salt foods, sugar, and starch (carbohydrates). This effort to "eat healthy" is in the media almost daily, and has received the attention and support of physicians, healthcare workers, educators, politicians and even the White House (Reference 1). These efforts have included increasingly demanding guidelines of nutrition for all age groups, including greater emphasis on improving school lunch programs and other institutional and commercial mandates. There is over-whelming support by healthcare professionals for increasing natural fiber and protein, while reducing starch and sugar (carbohydrate: CHO), calories and highly processed foods, all of which is critical in reducing obesity, diabetes, heart disease and cancer (References 2-7). Additionally, there is greater emphasis on plant-based protein which is far more sustainable and globally practical than large-scale production of animal protein. The push to reduce sugar, CHO, and processed foods, while increasing vegetables, whole grains and natural lean protein has contributed to the shift in school food programs and many other modifications to the eating habits of many consumers. Despite these efforts, the majority of food produced commercially still contains high levels of CHO (starch) with low levels of natural fiber and protein, particularly in flour-based baked goods, that includes but is not limited to pastries, cookies, cakes, breads, pasta, pancakes, waffles, pizza crust, muffins, bagels, etc. Efforts to artificially supplement flour, bread or soft-baked goods with added fiber and protein have dramatically and negatively changed the taste and texture of the product, which is why the majority of consumers defer to traditional products, in spite of their questionable nutritional value.

There has been much focus on increasing natural sources of fiber, protein (specifically plant-based protein), while reducing carbohydrates (sugar and starch). In the U.S. and Canada there is increasing demand for natural products that are devoid of highly-processed, artificial, or engineered ingredients; these are referred to as "clean-label" products. Ultimately the challenge is how to get the majority of the population to eat healthier, recognizing that the majority of the population will chose to eat food (particularly soft-baked goods and pasta) that has the taste and texture they prefer, regardless of whether or not is it necessarily good for them. Most consumers prefer the taste and texture of traditional (e.g., low-fiber, low-protein, high starch, high-sugar & highly-processed) baked goods, pastries, cakes, cookies, breads, muffins, pastas, etc. The key challenge has been, and continues to be, providing the many types of flour-based foods that most consumers prefer to eat, but with significantly higher natural fiber and protein, coupled with reduced starch/sugar (CHO) and calories, but without compromising taste, texture, aroma, and color that consumers prefer and demand from their favorite flour-based goods.

Additionally, the trend toward natural, organic, un-processed and non-genetically modified organism (GMO) food products—absent of artificial inputs and preservatives—has reduced the functional shelf-life of specialty and soft-baked goods, resulting in tremendous loss of product and revenue. For example, calcium propionate (Calpro) is added to flour to extend the shelf life of baked products from 3 days to between 10 and 14 days. Many other artificial preservatives are added in an effort to extend functional and practical shelf-life. Therefore, it can be appreciated that there is a significant need for a process that will generate ingredients to provide a natural way to extend the shelf-life of fresh-baked goods and have a tremendous impact on several specialty markets, particularly bakeries.

BRIEF DESCRIPTION OF THE SEVERAL VIEWS OF THE DRAWING(S)

FIG. 1 illustrates a table listing candidate substrate products usable in the conversion process described herein.

DETAILED DESCRIPTION OF THE INVENTION

Figure 2:
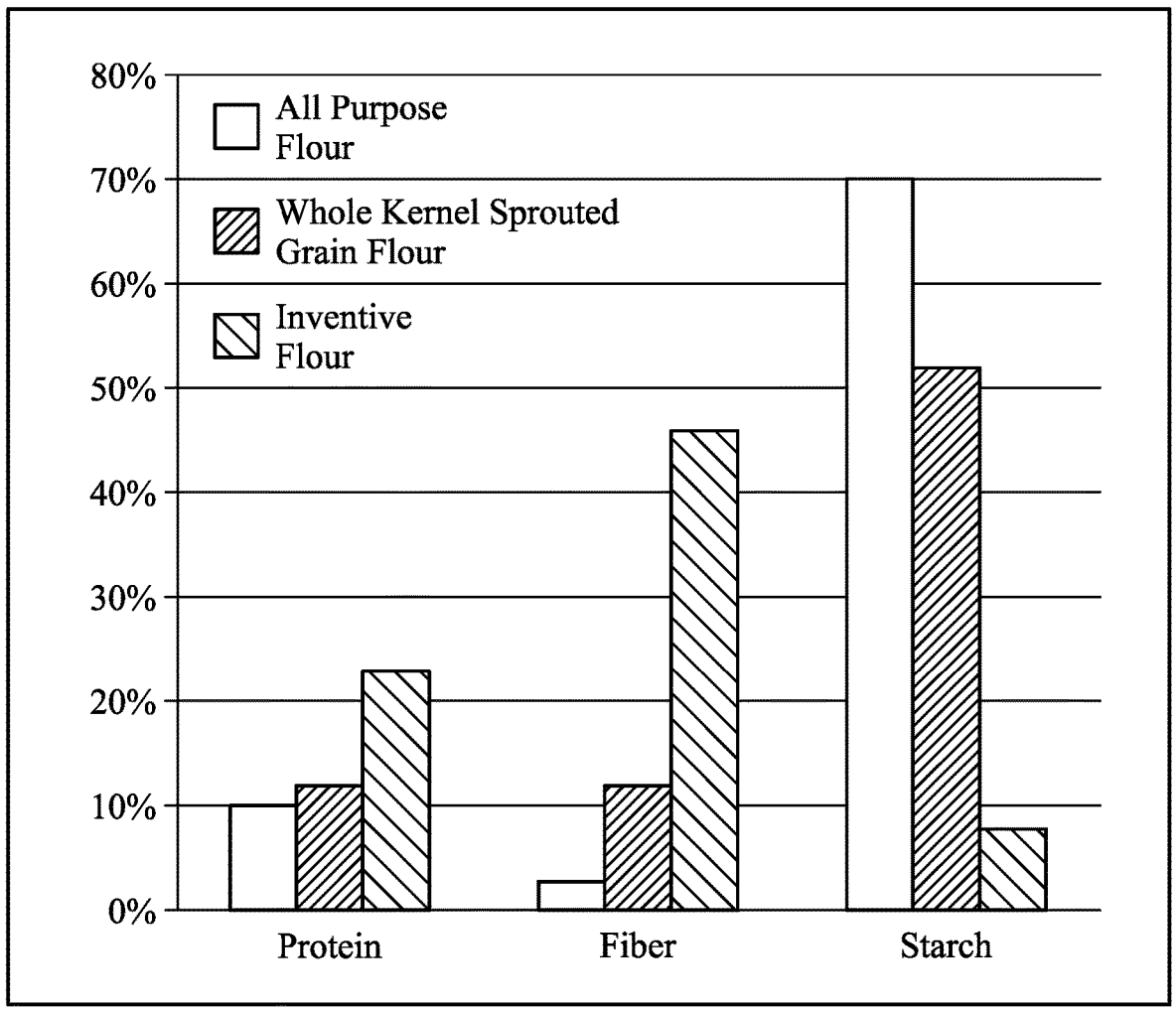
FIG. 2 illustrates a table and graph illustrating the characteristics of the inventive flour compared with all purpose flour and sprouted grain flour.

The present disclosure describes a process for the production of high fiber, high-protein, low-carbohydrate flour, cereals, sweeteners, and a sweetened liquid derived from a variety of substrate products, including, but not limited to, grains, seeds, beans and legumes, and root vegetables and tubers. As used herein, the term "substrate" refers to the initial ingredient or ingredients that are used in the creation of the inventive flour. Thus, any and all varieties and species of modern, ancient and heritage wheat, grains, seeds, beans, legumes, tubers, and root vegetables may all be considered substrates. As will be described in greater detail below, the characteristics of the inventive cereal, inventive flour, inventive sweetened liquid, and inventive sweeteners, depends on the selected substrate.

"Flour" is a generic term that describes a physical condition relating to the granular consistency and size of substance—both organic and inorganic. According to Webster's Dictionary, flour is both a noun and an adjective, citing "a product consisting of finely milled wheat; also: a similar product made from another grain or food product (such as dried potatoes or fish). It is also defined as a "fine, soft powder." Wikipedia defines flour as "a powder or dust, made by grinding raw grains or roots and used to make many different foods." Cereal flour is the main ingredient of bread, but flour is not limited to grains, seeds, cereals, etc. As used herein the term "flour" notes the finely milled consistency comprised of our inventive product and is not limited to wheat/grain-based substance to which the average consumer refers. The new type of flour prepared in accordance with the present disclosure is referred to herein as the "inventive flour." The inventive flour has very different characteristics than wheat-based "all-purpose" baking flour that is currently available in grocery stores today.

Certain portions of the process bear some similarity to the preparation of grains for fermentation into beer and/or distillation into spirits or ethanol/alcohol. However, there are key distinctions between the conventional fermentation process and the inventive process described herein. Those differences result in dramatically different end products having dramatically different characteristics. Nonetheless, it may be helpful to explain the fermentation process so that the differences may become clearer.

The fermentation of grains into beer, and distillation of beer into higher-proof alcohol or spirits has been around since at least the first century AD. In modern times the fermentation and distillation of grain-based mash continues as the basis of the alcoholic beverage industry, as well as for industrial bio-fuel (e.g., ethanol) as an additive to gasoline and other industrial purposes. In all cases, the fermentation and distillation process generate a solid waste product known as "distiller's grain." When dried, this is known as "dried distillers grain" or DDG. Whether produced from grain or corn, DDG has been used solely as an animal feed product, unsuitable for human consumption—especially DDG derived from corn-to-ethanol process.

Several efforts were made to improve the odor and texture of the fermented residues, particularly those based on wheat strains, with the goal of producing a potential human-grade food by-product (References 8-14). These attempts were generally unsuccessful since the process to produce ethanol employed powerful synthetic enzymes, yeasts; extreme pH and temperatures—all designed to maximize the conversion of starch to sugar, and then sugar into alcohol, with little interest or attention to the potential food product. Whether to produce bio-fuel (read ethanol), beer or spirits, the process is designed and geared toward fermented liquid and alcohol, not a food-based solids and liquids. Additionally, there has been little or no research on the potential quality and use of naturally saccharified grains, that have been carefully germinated, without any fermentation.

The proprietary process disclosed herein was derived from research and experimentation with processes and preparations of grain similar to those utilized by brewers and malters. However, instead of a process designed to produce fermented liquid, the focus was shifted to a process to develop new types of food products for human consumption that have unique enzymatic, nutritional, and sensory qualities—without fermentation. The present process separates, converts, and removes starch from grains, edible seeds, legumes, and root vegetables that have high starch content to create a flour with high protein, high fiber, enzymes, macro & micro-nutrients, and low starch and reduced calories. This process distinctly differs from standard wet-milling processes generally used to prepare ethanol and it differs from standard malting industry, which is generally used to maximize the malting process for fermentation of beer or spirits with no concern for food. In addition, it is an all-natural process eliminating artificial enzymes, chemicals, and harsh conditions (pH and temperatures) commonly used in alcohol production.

The process described herein is distinctly different from standard dry-milling processes generally used to process flour by milling whole, partial, sprouted or other-wise processed grains. This is because the process of the present disclosure is focused on dry-milling as only one step in a multi-phase inventive process. The present process utilizes controlled germination and natural conversion of grains and legumes so as to promote ideal conditions for the food and nutritional quality of the product. After controlled hydration, the converted grains and legumes are then either wet or dry-milled to expose the starch. These are then carefully processed at various temperatures during which endogenous amylases and added natural amylase (in the form of malted grains, seeds, or legumes) are used to stimulate saccharification in order to convert the starches to complex sugars. Once complete, the carbohydrate-rich liquid is separated from the solids, which are then dried and milled into an inventive baking flour that is extraordinarily high in fiber, protein and extremely low in starch. The flour has a number of unique and valuable characteristics in in terms of quality, flavor, texture, and aroma.

This inventive process is also distinctly different from standard malting processes generally used to prepare malted grains (malts) for fermentation and distillation to produce beer and spirits. Processing beer and spirits focuses on specific malting process to produce malted grains rich in amylase necessary for making beer and/or sprits with no regard for the food potential or quality of the wet distillers grain (WDG) or dried distillers grain (DDG). The focus is on fermentation and ethanol—not food. Additionally, the process of malting to produce malted grains has been limited exclusively to substrates (such as barley, wheat, oats, corn, rye, triticale, some rice, etc.) that are known to produce beer and spirits that are acceptable by the general public for consumption. Our inventive process is not focused on malting or malts to produce beer or spirits, but rather the controlled germination to produce unique food products.

This inventive process is also distinctly different from standard sprouting industry in which whole kernel of grains, rice's, beans, and legumes are fully sprouted then milled into baking flour or used in other consumer products such as cereal. In these cases, the fully sprouted whole kernel is used to capture nutritional benefits of sprouting. However, the taste, texture, aroma of products using sprouted grains and legumes do not share the positive qualities of our inventive flour. These products are coarse, dense, waxy, bitter and lend a quality to products that consumers associate with "high-fiber, high-protein". Often additional sweeteners and other additives are used to reduce the unpleasant taste and texture qualities of these products to make them more appealing to the consumer. However, these additives lend additional calories to the products as does the fact that all off the starch and carbohydrates remain. Our inventive process does not incorporate full sprouting, but rather controlled and limited germination. Additionally, we do not use the whole grain with all of its endogenous starch and carbohydrates, but rather our inventive process utilizes a gentle and multi-stage saccharification process to convert starch to sugars then separate this to produce a unique inventive flour extremely high in fiber, protein and low in starch, carbohydrates, and calories. This inventive process naturally produces products that when used in freshly baked goods or as a cereal provide distinctly high qualities of flavor, texture, and aroma, not seen with in other high-fiber, high-protein products.

Nor is this inventive process like the fractionated wheat or grain industry or process that are used to separate wheat (or other grain) bran, germ, protein, and flour (endosperm) for use in food and dietary additives. In these cases, the goals are to separate the higher-value portion of the grain (germ, bran, fiber, protein, etc.) from the lower value starch. The higher-value products are used for food-specific uses, and the lower-value starch is milled into all-purpose flour. However, the taste, texture, aroma, and baking qualities do not share the qualities of our inventive flour. The fractionated products are coarse, dense, waxy, bitter and lend a quality to products that consumers associate with "high-fiber, high-protein". Often additional sweeteners and other natural and synthesized additives are used to reduce the unpleasant taste and texture qualities of these products to make them more appealing to the consumer. However, these lend additional calories to the products. Nor do these products increase the shelf-life of natural soft-baked goods. Our inventive flour is not bitter and baked goods using our inventive flour are not dense, coarse, waxy, etc. Other than a slight darkening of the soft-baked goods, they remain light, fluffy, sweetly aromatic with enhanced flavors. Consumers do not detect the negative characteristics associated with "high-fiber, high-protein, reduced-calorie" products. This is because our process uses a unique and hereto undiscovered process for carefully and naturally converting ancient, heritage and modern grains, seeds, beans, and legumes to produce products that have a unique characteristics and qualities. In addition, the conversion and saccharification process can be applied to tubers and root vegetables as well. In all cases the products exhibit unusually high qualities for taste, texture, aroma, as well as natural extension of shelf-life for baked goods.

To date, testing and verification of these processes, products and nutritional benefits have been limited to small-scale production, commercial testing, and personal use. However, one skilled in the art can appreciate that the processes described herein are readily scalable to large-scale commercial production levels.

This proprietary process and methodology have been accomplished (with product-specific variations) with various varieties of wheat, rice, beans, legumes and root vegetables and are adaptable to many other ancient, heritage and modern grains, seeds, legumes, root vegetables and tubers. This process or minor modification thereof, can be used to create "inventive flour", "inventive sweetened liquid", "inventive cereal" and "inventive sweeteners" from many different initial substrates. These substrates include, but are not limited to, those listed in a table illustrated in FIG. 1. To support the proof of concept, the disclosed process has been applied to Soft White Winter Wheat, Hard Red Wheat, Brown Rice, Jasmine Rice, White Jasmine Rice, Great Northern White Beans, Lentils, Carrots and Russet Burbank Potatoes. The description of this process is provided below.

Carbohydrate in grains comes in two forms, starch, which is a metabolically available source of energy for humans, and fiber, which is not metabolized by humans. An important difference between them is that starch has chemical bonds between the sugars that can be hydrolyzed to monosaccharides by human enzymes (and thus, the sugars can be used for energy) while the bonds between the sugars in fiber cannot be hydrolyzed by human digestive enzymes.

For comparison purposes, the characteristics of the inventive flour are compared with conventional flour manufactured from a sprouted whole kernel wheat and with a widely available commercial all-purpose flour (APF) from the local grocery store as the representative common store-bought flour for most baked goods. In a recent production run, the sprouted whole kernel wheat and the inventive flour were both produced from soft-white winter wheat. The inventive flour contained approximately 23% protein (230% of the protein found in the APF), 46% fiber (1500% of the fiber found in the APF) and 8% CHO (9% of the CHO found in the APF) as illustrated in a table in FIG. 2. The same data is also illustrated in graphical form in FIG. 2. These are composition metrics that have never been observed previously in any flour. The percentages of protein and fiber may increase further depending on the specific variety or type of substrate used. For example, a wheat variety (such as hard red) or bean that has a starting protein level higher than soft white winter wheat, will result in even higher protein and fiber content.

In a typical baking process, displacing 50-100% of standard wheat baking flour (APF) with the inventive flour provides substantially higher fiber and protein, and reduced starch and calories without significantly changing the taste, texture, and aroma of the baked product, and in many cases, improves the quality, taste, and texture. In no case does the use of the inventive flour result in the rough, waxy, coarse, dense, and dry texture and unappealing taste qualities associated with many "high-fiber" and higher-protein baked products. Additionally, the process disclosed herein can produce and provide increased nutritional and dietary advantages to pet food (e.g., dog, cat, and equine food), particularly on a breed and performance-specific basis, through the addition of the inventive flour derived from selected and blended substrates.

Further, the present disclosure describes a process for making a sweetened liquid that is high in CHO (maltose and other complex sugars depending on the selected substrate), and moderate levels of protein and fiber which is suitable for energy drinks, smoothies, nutrition bars, protein bars and other products. This liquid can be reduced to thick syrup, with toffee-like consistency, or a solid which can be ground into powder to produce a crystalline sweetener.

If one takes the mash that has been treated to remove the starch (through Step 7 in Process I, below) and dries the mash, the resulting material can be either ground to produce the inventive flour or used as a naturally sweet granola type "breakfast" cereal or made into snack bars that are high in fiber, protein, nutrients and low in starch (but contains some maltose and other complex sugars depending on substrate).

The same basic procedure has been used for multiple varieties of wheat (soft white, hard red, durum), rice (white, jasmine, and brown), beans and legumes (Northern White Beans, Lentils, Peas), with substrate-specific adjustments in incubation times and temperatures to produce the inventive flour from these substrates in proof of concept preliminary laboratory production experiments. Further, carrots and potatoes (tubers and root vegetables) have been grated and treated with the amylases to produce the inventive flour and inventive sweetened liquid in proof of concept laboratory-scale experiments. Thus, we have demonstrated the versatility and breadth of this innovative technique for reducing starch in these substrates and thereby producing the inventive flour that is enriched in proteins, fiber, and other nutrients, as well as unique qualitative characteristics of taste, texture, aroma etc. There is no evidence to suggest that this process cannot apply to virtually all such substrates including all ancient, heritage and modern grains, seeds, beans, legumes, tubers, and root vegetables.

Composition of the Inventive Flour and Inventive Sweetened Liquid

Analysis of the composition of the inventive flour produced from soft white winter wheat by a contract food analytical laboratory is shown in the table of FIG. 2. Again, we have use APF white flour as flour that represents common grocery store products that can be purchased today. These data are representative of the inventive flour (derived from Soft White Wheat) analysis and have been reproduced in other such analyses. It should be noted that using higher-protein substrates, such as hard red wheat or legumes will result in higher protein content of both flour and liquid.

Figure 3:
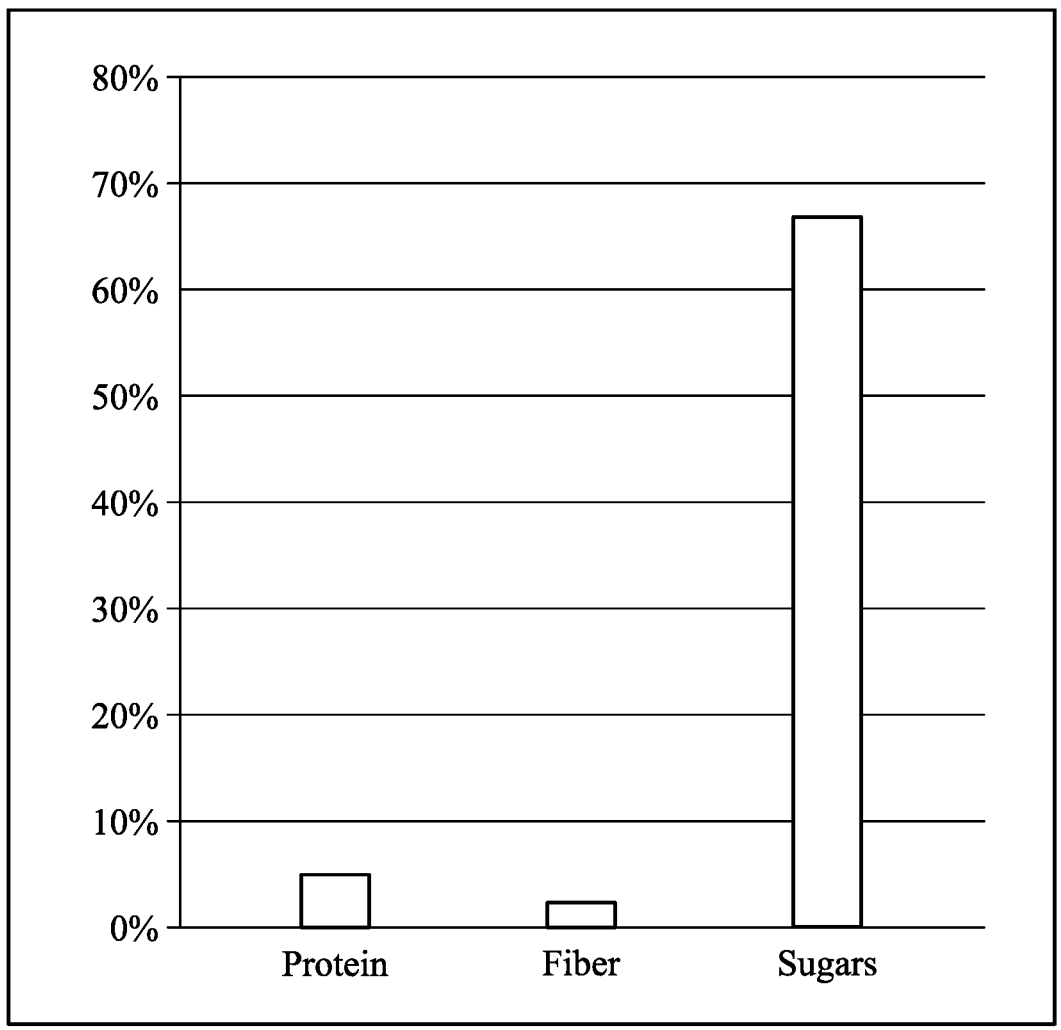
FIG. 3 is a chart illustrating the comparative levels of protein, fiber, and sugars in the liquid portion of the inventive products.

Along with the "eat healthy" attitude in the USA is the "live healthy" attitude that brought the triathlete and extreme exercise philosophy. This active exercise lifestyle requires energy drinks to maintain the fluid, carbohydrate (CHO), protein and fiber levels to support the extreme endurance requirements. Additionally, the strong recommendations for whole, unprocessed foods rich in natural plant fiber and protein compliment this trend. The sister product of the inventive flour process is a high-CHO liquid with moderate levels of protein and fiber, ideal for energy and performance drinks that has the much-needed energy and nutritional elements to support the extreme energy demands of these athletes. The term "inventive sweetened liquid" as used herein refers to the liquid extract that results from the processes described herein. While many of the available energy drinks today are a simple mixture of water, some added electrolytes and processed sugar, the inventive sweetened liquid is a completely natural product with no artificial additives and greater nutritional value. Depending on the selected substrate and the selected process, the inventive sweetened liquid extract made from a starch containing substrate, such as grains, beans, legumes, or root vegetables/tubers, will have varying percentages of protein, fiber, and sugars. The inventive sweetened liquid derived from soft white winter wheat has approximately 3-7% protein, 1-5% soluble fiber and 60-70% sugars. The chart of FIG. 3 illustrates an example composition of protein, fiber and sugars in the inventive sweetened liquid derived from a soft white winter wheat substrate product. It should also be noted that the separation process can be varied to allow for higher or lower amounts of transferrable protein and fiber. The sugars will remain constant.

Example Embodiments of the Disclosure

The following is a detailed description of the process and procedure used for soft white winter wheat and hard red wheat. In addition to the description for wheat, the detailed description includes the process and procedures for rice, beans, and lentils; as well as carrots and potatoes (with variation that does not include the controlled germination). Soft White Winter Wheat was chosen as the primary substrate for its superior food-grade quality, high starch content and local availability. The processes described will generally work on any edible ancient, heritage or modern grain, seed, or legumes, so long as the seed, grain or legume has process-specific characteristics. For example, the grains, seeds legumes can undergo a natural germination cycle that can be naturally stimulated in a specific environment; at a specific temperature over a specific period and that this controlled germination stimulates the natural production of enzymes as well as other endogenous and native transformations. Although a root vegetable (e.g., potato or carrot) is not germinated in the manner described above, these tubers can go through the saccharification process to remove the starch to yield concentrated protein, fiber and micronutrients providing unique and specialized properties as a result of this process.

Base Requirements, Information & Assumptions

Wheat is measured in bushels. Each bushel weighs approximately 60 pounds at approximately 13.5% moisture. There are approximately 33.3 bushels per ton.

Premium Malted Barley is rated "malting-grade". There are approximately 48 pounds per bushel of barley. There are approximately 42 bushels of barley per ton. Barley is measured in tons. Un-malted barley can be fully malted, or it can be purchased already malted, graded, and certified.

No. 1 quality soft white winter wheat should be used with a minimal amount of dirt, straw or other non-kernel contaminates. The grain should be sourced from reputable suppliers who provide top-grade sorting, cleaning, and packaging.

Premium quality malted barley should be used with a minimal amount of dirt, straw or other non-kernel contaminates. This should be sourced from reputable malt suppliers who provide top-quality product that has been fully tested and certified.

Any other grains or legumes should be rated No. 1 top quality, having been sourced from reputable suppliers who provide top-grade sorting, cleaning and packaging with a minimal amount of dirt, straw or other non-kernel contaminates.

Figure 4:
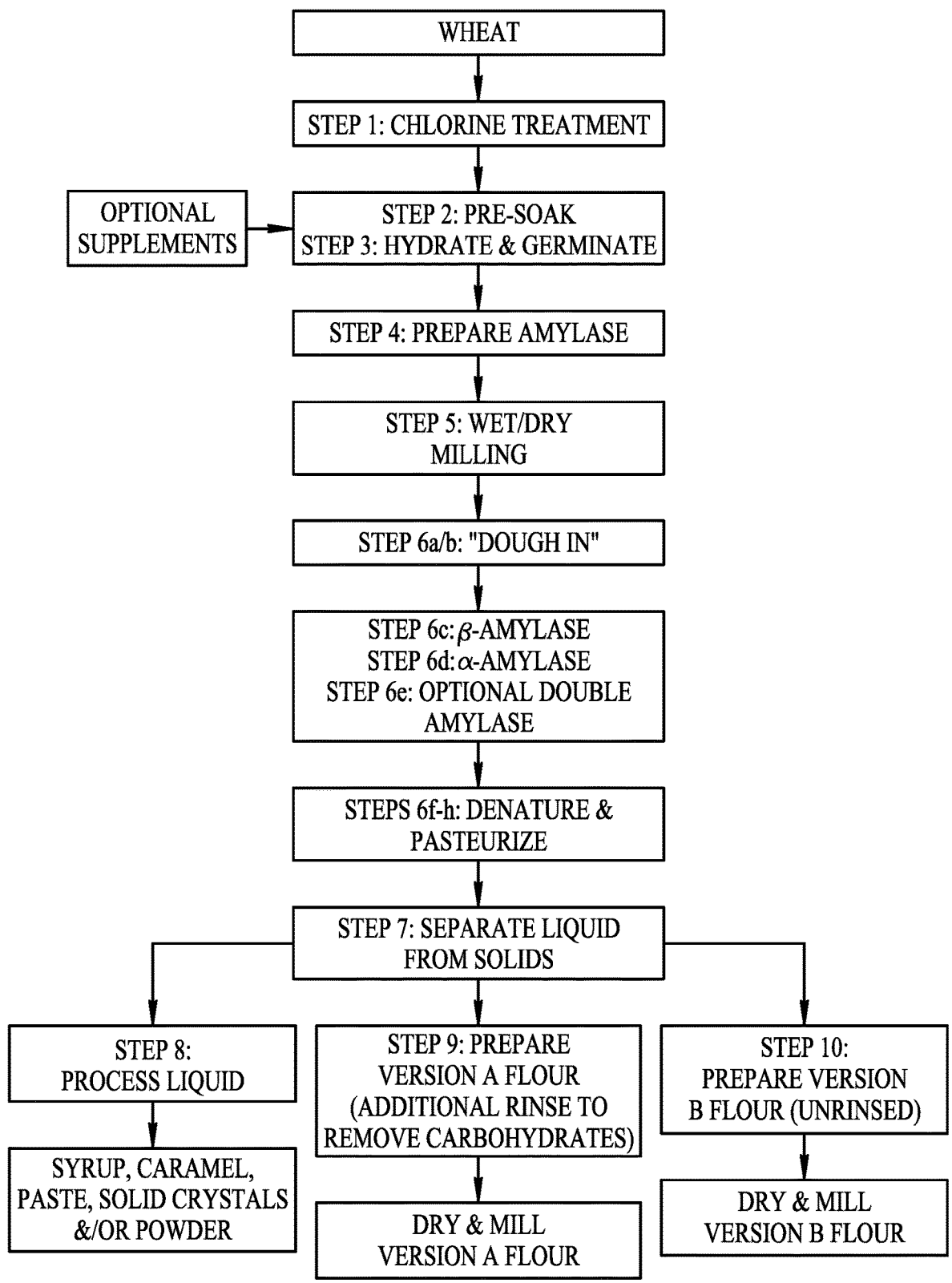
FIG. 4 illustrates a process diagram as applied to wheat as a substrate.

Several versions of the inventive flour are disclosed. The process for Versions A and B is the same except for a difference in a rinsing process. Version A inventive flour has a lower carbohydrate content than Version B inventive flour because Version A mash is rinsed with additional water to remove residual sugars. With the different rinse processes, the inventive sweetened liquid from the different versions is also slightly different. Version A inventive sweetened liquid has a slightly higher carbohydrate value than Version B inventive sweetened liquid. Version C inventive sweetened liquid uses a different milling process. The different versions will be discussed in greater detail below. FIG. 4 illustrates the process as applied to wheat.

It should be noted that the inventive flour differs in weight from standard all-purpose flour (APF). As a general comparison, APF and whole grain flour (WGF) is ~154 grams per cup. Inventive flour Version A (rinsed) flour is ~106 grams per cup and the inventive flour Version B (unrinsed) is ~126 grams per cup. However, when properly used, the inventive flour displaces standard APF by volume, not weight. For example, if there is a soft-baked product requiring 2 cups of APF, then 50% of the APF (1 cup) will be displaced with the inventive flour (1 cup).

Regarding the question of ratio from whole kernel to processed inventive flour: the approximate ratio of whole kernel wheat to inventive flour is as follows:

a. Inventive Flour, Version A (Rinsed) 106 grams/cup: 10 pounds of whole wheat produces approximately 4-4.5 pounds of the Inventive Flour, Version A (rinsed) or approx. 5-5.5 pounds of the Inventive Flour, Version B (unrinsed). This has the effective equivalent of 5.9-6.6 pounds per volume weight of Version A (rinsed) and 6.25-6.9 pounds of Version B (unrinsed) as compared to standard flour. This is because inventive flour displaces regular flour by volume, not weight. Because the weight to volume ratios is significantly less for the inventive flour than standard flour, this must be factored into the calculation of utilization values.
   b. The weight to volume is less given the starch content of the whole germinated grain kernel is 52%, and the process converts approximately 92% of the starch to complex sugars, which are then removed from the inventive flour.

Process 1 (See FIG. 4)
Inventive Flour Process Using Grain (Versions A & B) Using Soft White Winter Wheat & Malted Barley:

Step 1—Cleaning the Grain to Remove Debris & Contaminants a. Utilize clean, No. 1 soft white wheat with no evidence of field sprouting. This should be thoroughly sorted and cleaned by the supplier to remove any residual dirt, debris, etc. However, the quality of the final product may vary slightly as part of the process plant's equipment and pre-cleaning process.
   b. Immerse the wheat for approximately five minutes in a mild Chlorine solution (70-100 ppm active ingredient) in order to kill most adhering bacteria, toxins or residual contaminants that are naturally present in grain or surrounding material.
   c. Rinse wheat with clean water and test so that no residual Chlorine remains.
   NOTE: The optimum Chlorine ppm appears to be 75-100 ppm, but other concentrations may be acceptable.

Step 2—Pre-Soaking Wheat a. Pre-soak wheat in a clean water solution, making sure it is completely submerged for a total of 10-14 hours at 55-70° F. to stimulate initial germination. For the purposes of this process, the soaking time was 12 hours and the temperature used was 65° F. for germination. Flush water and re-submerge wheat with fresh water every 2-5 hours, gently stirring the wheat upon water changes to ensure oxygenation and equalization of temperature and solution. Ideally this should include 3 complete water-change cycles.
   b. Maintain relatively constant temperature throughout the soaking period/immersion period. In addition, gentle mixing or stirring should be introduced to ensure proper oxygenation and to prevent "hot spots." To maintain temperature, cycling fresh water through this cycle may be required. Other mechanical temperature control mechanisms may also be utilized.
   NOTE: At this stage fortifying the pre-soak water solution/medium with iron, or other water-soluble minerals, salts, vitamins, or nutrients can be added in order to enhance the grain and final product nutrient content. The soaking grain will absorb a portion of those water-soluble nutrients. This process provides the potential for customizing the nutritional properties of the end product and develops the possibility of novel/customized nutraceutical products and ingredients.

Step 3—Germination a. During the final germination phase, the wheat is no longer submerged in water, but is rather rinsed to maintain full hydration. The water is drained, while keeping the wheat hydrated with water rinses every 2-4 hours with gentle mixing in a covered container. As an alternative, the hydrated grains can be spread out to a consistent depth of 1-2" in stainless trays, and then sprayed frequently with cool tap water (60-65° F.) and covered with a moist cloth, although the final process will be determinant on the scale of production. If small portions of grains are being germinated, for example, less than 10 pounds at a time, the hydrated wheat can be held in a container at a depth of up to 12-16", so long as the pile is rinsed with cool water and gently stirred on a regular basis. Frequent rinsing and draining of the water every 2-4 hours prevent "drowning" the wheat. At this point none of the wheat should be fully submerged in water. The hydrated wheat must be occasionally mixed to ensure proper oxygenation and to prevent "hot-spots," while maintaining consistent hydration and temperature. During this period, it is imperative to maintain cleanliness and general temperature control to ensure consistent germination and minimize chances for contamination and excess sprouting which will adversely affect the quality and taste of the final product. It should be noted that this process is for controlled germination not fully sprouted or malted grains. The controlled and limited germination of the present disclosure provides unique nutritional, textural and taste qualities non-experienced with fully sprouted or malted grains.
   b. The germinating grain must be washed/flushed and rotated periodically throughout the germination period to provide consistent temperature control and thorough hydration throughout the batch. This also provides a consistent temperature throughout the batch, while counteracting the natural respiration process that will generate heat or "hot spots." This rinse may contribute the fact that the high-fiber flour lacks the "bitterness" that is associated with other high-fiber products, although this has yet to be determined.
   c. Typically, adequate germination occurs within 12-24 hours after the initial 12-hour soaking/submersion phase, depending on wheat, temperature, humidly, elevation, etc. Lower temperatures may result in a longer germination period. The warmer the condition, the faster the germination, although temperatures greater than 74° F. are not advised. Careful monitoring at this stage is critical so as not to go beyond the initial batch-wide germination to the point where 1) the average spout tails or acrospires become longer than ¼-⅓ the length of the seed—although a percentage will be at ⅓ the length since it is impossible to control absolute uniformity. In a small portion of the pile, the early "bud" may only start to be visible in some of the kernels. The goal is to obtain a germination stage that is consistent and average throughout the pile. In some applications, one skilled in the art may permit the acrospires become approximately the length of the seed. However, there is a point where longer germination periods will begin to affect the taste of the substrate product. This can vary from one substrate to another.

At no point should the grains be taken to full sprouting or malting. Should this happen the quality of the batch is adversely affected as the final product will have a "dirt-like," "bitter," or "grassy" taste. Research has confirmed that initial germination is important to strike a balance between amylase production while maintaining the favorable taste quality and protein content of the grain, particularly since fermentation is not a goal. It should be noted that virtually no prior research has been done to show the potential or benefits of controlled germination for the purposes of producing superior food products. The ideal condition of initial germination is when the hull has opened, and the first signs of the germinating "bud" occurs and the acrospires has grown to a length no longer than ¼-⅓ the length of the kernel.

d. During this phase, cleanliness and quality control is critical to prevent the contamination from microorganisms or toxins. Malt houses go through these steps but are not as concerned about some of the environmental conditions that concern us, since sprouted grains intended for malting are first dried to stop further sprouting and enzymatic production, then roasted at much higher temperatures since they are intended for fermentation, not food production. Malting houses often roast the grains (after the initial drying) at temperatures exceeding 200° F. or higher to produce darker barley desired in many beers. This will kill off any contaminating microorganisms. The process of the present disclosure does not use a high-temperature heat process, since this may alter the nutritional value of the products and may introduce tastes that are not intended for our final product. The "cooking" process includes a denaturing and pasteurization stage. The germinated grains are dried at a temperature of 110° F. in order to put the kernel into dormancy without denaturing the activated enzymes, particularly the β- and α-amylase. Once the kernels are dried and the activated enzymes are put into dormancy, the kernels continued to be dried at a temperature of 120-125° F. to a moisture content of 7-10%

NOTE: The exception to this rule is Version C which utilizes malted wheat as a substrate material (see details under inventive flour Version C).

Step 4—Preparing the Malted Barley Amylase a. Utilize clean, #1 or highest premium pale malted barley from a reputable supplier. No barley that has been roasted to a darker color should be used as it will affect the color and flavor. This must be brewer's grade malted barley.

NOTE: Although illustrated in FIG. 4 as Step 4, those skilled in the art will appreciate that the amylase preparation can occur at any time prior to the introduction of the amylase in Step 6 below.

Malting the barley from scratch is also an option, but not necessary since brewer's-grade malted barley is standard amylase and has the incumbent quality control.

b. Mill the malted barley into the consistency of "bread-grade" flour. This will provide the β- and α-amylase for the saccharification process for starch to sugar conversion.

c. The ideal ratio of malted barley is 8-10% barley to 92-90% wheat measured on a dry weight, i.e., before the hydration of wheat. For example, if 10 pounds of dry wheat is being prepared, then mill up to 1 lb. of malted barley.

NOTE: Those skilled in the art will appreciate that the percentage of malted barley could be as low as 5-7%, but this remains to be validated and the benefits of a lower percentage quantified. Those skilled in the art will appreciate that the amount of barley (or other amylase source) can vary based on the characteristics of the substrate (e.g., wheat versus potatoes versus beans). The amount of barley (or other amylase source) could vary in a range of 5%-50% (on a dry weight) of the amount of substrate.

d. In applying the malted barley flour as part of the process, take malted barley and dry mill into a fine bread flour consistency; sift it through a fine flour sifter to remove hulls, sprout tails and other particles and to yield a finely dispersed barley flour. To the suspension of milled, germinated grain, add 10% dry milled barley flour in ⅓'$d$ increments at 15 min intervals. For example, for 30 pounds of milled, germinated grain, you would add 3 pounds of malted barley powder in 3 separate 1-pound increments. After the initial low-temperature "dough-in" (110-115° F.) of the mash, the mash temperature is increased to 134-135° F. and held for 1 hour with constant gentle stirring, during which the malted barley flour is added every 15-minutes in ⅓ increments after the initial 15 minute period. After the barley flour is introduced, the mash temperature is slowing increased to 150-160° F. and held for 45 min. Finally increase the temperature to 200° F. for 10 min to pasteurize the mixture (killing any organisms that may reside in the grain and denature any residual enzymatic activity to stop the saccharification process.

Step 5—Milling

The milling process can be a wet milling or a dry milling process, each of which is described below.

Step 5a—Fracturing, Tearing or Shearing the Germinated Grain: Wet-Mill Option 1 a. After cleansing, hydration and germination is complete, the wheat hull must then be fractured or sheared in order to expose the inner-grain to the native and added β- and α-amylase during the cooking process. The process must mechanically cut the hydrated and germinated grain. Hydrated and germinated wheat is quite resilient and standard mechanical presses may not work. The key is to expose the kernel without completely pulverizing the grain. If the grain is too pulverized before the cooking process, particles may become so fine that it is difficult to screen or separate them from the sugar solution following saccharification.

NOTE: Currently this wet-milling or fracturing process has been accomplished by using a die-head-type meat grinder, using a two-stage number 7 (7 mm) die-head and then a number 4 or 5 (4-5 mm) die-head. This mechanically cuts the germinated grain without pulverizing the grain. This type of grinder does leave a small percentage of whole seeds, even using the 2-stage process, thereby artificially increasing the starch content in the final product. To date it appears that running a two-stage process using a 7 mm and 4-5 mm die-heads works well, although alternative means and equipment for the wet-milling stage may be applied to ensure 100% of kernels are fractured. Large batch or industrial-scale process plant can readily employ commercial tools, such as a specially designed dual corrugated rolling/crushing mill that has been specifically designed for hydrated wheat—one that will expose the kernel without undue pulverization. Another option is to utilize a dry-milled process for cracking or fracturing the grain (see below).

Step 5b—Fracturing the Germinated Grain: Dry-Mill Option 2 a. After cleansing, hydration and germination is complete, the wheat hull must then be fractured or sheared in order to expose the inner-grain to the native and added β- and α-amylase during the cooking process. The hydrated and germinated grains are dried at a temperature of 110° F. in order to put the kernel into dormancy without denaturing the activated enzymes, particularly the β- and α-amylase. Once the kernels are dried and the activated enzymes are put into dormancy, the kernels continued to be dried at a temperature of 120-125° F. to a moisture content of 8-10%. The germinated grains are then dry-milled in a grain cracking mill set to approximately 0.25 or similar setting to ensure the complete fracturing of all dried germinated grains. The results of the dry-milled product have been excellent with consistent results in producing the inventive flour.

Step 6—Cooking the Wheat/Barley Mash:
 a. Heat the water to 110-124° F. prior to adding the fractured hydrolyzed wheat. The volume of water should be 1-1.5 quarts of water per 1 pound of dry wheat depending on the desired thickness of the mash. In an exemplary embodiment, 124° F. was selected and a water to dry wheat ration of 1.25 quarts of water per 1 pound of dry, cracked wheat. The objective is to have a thick mash similar to a thin or "watery" oatmeal cooked cereal.
 b. Dough-In phase: At 124° F. add the wheat and mix thoroughly. Introducing the cooler wheat, will reduce the entire mash temperature to approximately 104-114° F. Cease any heating and let the mash sit for approximately 30-45 minutes with occasional or constant gentle mixing to ensure the complete saturation of starch within the water & mash. After the first 20 minutes, it may be necessary to reheat the mash to approximately 104-114° F. should the temperature drop below 95° F.
 NOTE: At all stages of heating, it is critical to ensure that no scorching occurs to the mash. Overheating and scorching tends to darken the color and could ruin the aroma and flavor of the product.
 c. β-Amylase phase: After the dough-in phase, raise the temperature of the mash to 133-136° F. and hold for 15 minutes gently stirring constantly. In an exemplary embodiment, 134° F. was used for the β-amylase phase. After the first 15 minutes add ⅓ of the malted barley flour, making sure that it is thoroughly mixed. Add this by sifting the barley flour into the mash while gently mixing it into the mash. Use a fine screen sifter to ensure the residual malted barley spout tails are prevented from being mixed with the mash. This will help to prevent a bitter taste to the product. Ensure that there is a complete mixture of the amylase flour within the mash and that the barley flour does not congeal or "dough-up" into non-mixing nodules. After each 15-minute interval, add an additional ⅓ of the malted barley flour following the same application process and protocol as before. After 15 minutes of constant gentle stirring, add the final ⅓ of the malted barley flour, following the same application process and protocol as before. This phase optimizes the β-amylase conversions.
 d. α-Amylase phase: At the end of the β-amylase phase, increase the mash temperature to 155°-160° F. In an exemplary embodiment, a specific temperature of 155° F. was used. At this point hold the temperature of the mash steady for 35-45 minutes with constant, gentle stirring/mixing. Gentle mixing ensures constant temperatures throughout the mash, without stressing the solids. As all of the Malted Barley flour has already been added, the temperature range in this step activates the α-Amylase that resides in both the malted barley flour and the germinated wheat. It also optimizes the α-amylase conversions and maximizes saccharification of starch to sugar conversion, particularly given the β-amylase preparation & conversions.
 e. The "Double Amylase" treatment: An optional modification to the procedure is to add the malted barley powder in 2 increments. During the saccharification process, starch is degraded to monosaccharides, disaccharides, and trisaccharides. As the concentration of these digestion products increase in the mash, they inhibit the amylases activity, so removing these saccharides improves the saccharification process. Thus, in step c (above), a total of 15% by weight portion of malted barley flour is added in 2 increments of 10% malted barley flour and 5% malted barley flour, with the temperature and incubation time the same as described, but without the final 200° F. step. Then the mash is pressed to separate the liquid and solid phases. The solid phase is re-suspended in water, as described in step 2, and the temperature is brought to between 150-160° F. The second half of the additional 5% by dry volume of malted barley flour as added to the mash and incubated at 150-160° F. for 45 min, then increase the temperature to 200° F. for 10 min to pasteurize the mixture (killing any organisms that may reside in the grain), kill residual enzymatic activity, and stop the saccharification process. The mash is pressed again, combining the liquid phases as described above. The solid phase is dried as described in step 4.
 f. Denaturing the Amylase & Pasteurizing phase: The wheat/barley mash containing the active enzymes must be denatured and pasteurized.
 After the 45-minute α-amylase stage is complete, slowly heat the mash to 198°-200° F. while stirring constantly. This will ensure a constant temperature throughout the mash and prevent scorching. As the mash temperature rises, the final saccharification will occur up to approximately 175° F. Heating the mash to 198°-200° F. will denature any remaining amylase, as well as pasteurize the mash to destroy any bacteria of toxins that may have contaminated the product as a result of preparation, germination, or handling.
 h. Once the mixture reaches a 198°-200° F. as a constant throughout the mash, hold this temperature for 5-10 minutes then stop heating and let the mixture set for a cool down period to a safe handling temperature of approximately 125°-135° F. Periodically mix the mash throughout this cool-down stage.

Step 7—Separation of Liquid (Inventive Sweetened Liquid) from Solids:
 a. At this stage, the separation methods will make it possible to control the composition of the final flour product to specific specifications, depending on the respective content requirements of the final solid and inventive sweetened liquid products.
 b. A sequentially finer mesh screen will proportionately decrease the solids that pass through with the liquid and will impact the final mass and characteristic of the flour. If additional pressure is applied in the separation process, this will also affect the final product characteristics. In addition, continuous flow centrifugation may be useful. The final process can be modified to achieve the desired output for specific versions of the inventive flour and inventive sweetened liquid.

c. Once the pasteurized mash has cooled down to an acceptable handling temperature, separating the liquid from the mash can be accomplished in any number of ways depending on the size and scale or the production/operation. These can include:
  i. Screened press
  ii. Solid/Liquid Separation by Centrifugation
  iii. Solid/liquid pump separator or stillage de-watering equipment Step 8—Preparing the Liquid Inventive Sweetened Liquid
  a. The inventive sweetened liquid that is separated from the solid processed substrate will have a varying consistency, depending on the thickness of the mash prior to separation. Typically, it has a consistency similar to syrup. It is comprised of a solution of water containing sugars (mono- di- and tri-saccharides), protein, soluble fiber, and micronutrients. These solids will settle or stratify if left sitting undisturbed for a period of time. The inventive sweetened liquid has a pronounced sweetness to the taste along with a slight malted flavor mixed with the taste of sweet, freshly baked bread.
  b. This liquid can be processed to reduce weight and volume by heating the solution in order to remove water or by vacuum evaporator or a microwave evaporator. Depending on the amount of water removed, this can produce a consistency of a very heavy syrup or honey, a thick caramel, or an extremely thick taffy-like consistency.
  c. If all the water is removed from the liquid phase, a solid that is similar to hard candy is produced, after which it can then be ground to into smaller crystals or sugar-like powder. The solid has a very pleasant and relatively mild sweetness with other pleasant residual flavors associated with the protein and fiber. At the caramel and solid phase there is no further stratification or separation of the non-sugar solids.
  d. In all instances the end product will contain mono-, di- and tri-saccharides (mostly maltose), fiber and protein along with other micro-nutrients. The final moisture content depends on the degree of reduction/evaporation.
  e. The rinse water that is captured as part of producing Version A Flour contains a 3-5% solution of maltose sugar. This can be distilled down to a solid crystalline sugar that is extremely sweet and quite flavorful.

Step 9—Preparing the Inventive Flour Version A
  a. Inventive flour from Grain, Version A is flour that is extremely high in fiber by volume (46%), high in protein (24%+) by volume, with significantly reduced/minimal starch (8%), calories and sugar. It is neutral in taste and aroma.
  b. Once the liquid is separated from the solid, as described in Process 1, Step 7 above, the remaining solids are thoroughly rinsed with water to remove residual sugars and other non-adhering fractions flushed off through a fine mesh screen. The goal is to retain a solid that has maximum fiber and protein and minimal starch and sugars.
  c. Once the rinse is complete, excess water is removed from the solids by either a screen press or a solid/liquid separation centrifuge.
  d. The remaining solids are completely dehydrated to approximately 7-10% moisture at a temperature of 115°-135° F. A lower temperature prevents caramelization and darkening of the solids and resulting flour. In an exemplary embodiment, 135° F. was used for the first 8 hours, and then 115° F. for the remaining 6-8 hours. Actual drying time will vary depending on the dehydrating equipment and moisture content of the solids, as well as other variable conditions such as ambient temperatures, humidity and elevation. In all cases, the final product should be dried until the desired moisture content (7-10%) is achieved.
  e. Once dried, the solids can be milled to "pastry-grade" or extra-fine grade flour, at which time it can be packaged, stored, and shipped.
  NOTE: Milling the product to a very fine pastry-grade consistency flour has shown to provide the best mixing characteristics in displacing standard all-purpose flour.

Step 10—Preparing the Inventive Flour Version B
  a. Inventive flour from Grain, Version B is made by exactly the same protocol as Version A (above), with the following exception: after separation of the liquid and solid phases (Process 1, Step 7, above), the solid phase is not subjected to an additional water rinse to remove residual carbohydrate, protein, fiber, and micronutrients (Process 1, Step 9, above). The liquid phase and solid phase are process as described in Process 1, Steps 8 and 9, respectively. The resulting liquid phase is slightly lower in carbohydrates and micronutrients while the solid phase, when ground to inventive flour, is slightly sweeter. It is a richer flour than Version A and is a superb enhancer of flavor, aroma, and texture, particularly when used in higher percentage of flour displacement (up to 100%) in baked products.

Process 2 (See FIG. 5)
Preparing the Inventive Flour Version C

We tried fully-malted Soft White Winter Wheat in two forms. Form 1 was a commercially purchased malted Soft White Winter Wheat and the other form was our own fully-malted Soft White Winter Wheat that we malted ourselves. This is in contrast to the standard germinated wheat/grain process. In both cases the malted wheat was put back into dormancy and properly dried to prevent denaturing of the amylase enzymes produced in the malted grain. Following the same process and procedures described in Version A and Version B (see above) we used the dry-milling process (described in Process 1, Step 5b) to crack the grain prior to creating the mash and "dough-in" for the "cooking" and saccharification process. Alternatively, a wet milling process may be used on the malted wheat as described in Process 1, Step 5a. We added the 10% malted barley flour to assist in the saccharification as well as to provide a standard template for comparison and measurement of our product—both the inventive flour and the juice and sweeteners. We found that our inventive process produces a high-quality flour and juice, but the taste profile of the inventive flour using malted wheat was slightly different than our standard inventive flour using germinated wheat. There was no bitterness to the flour, but it added a slight "malty" taste to the soft-baked goods, which may or may not be a desirable outcome. This confirmed that our inventive process is unique and can be applied to a wide range or grains in all forms including fully-malted grains. The inventive flours have many advantages, but that using our germinated process produced the most superior, neutral-tasting product. However, should a more pronounced taste profile be desired, fully-malted wheat can be used.

Additionally, in order to determine whether or not the process applied to Soft White Winter Wheat could be used for other substrates listed in the table of FIG. 1, proof of concept laboratory scale experiments was performed on another grain (rice), legumes (beans and lentils) and root vegetables (carrots and potatoes). In all cases, with certain substrate specific variations as noted below, the process proved successful in producing inventive flour and inventive juice.

Figure 5:
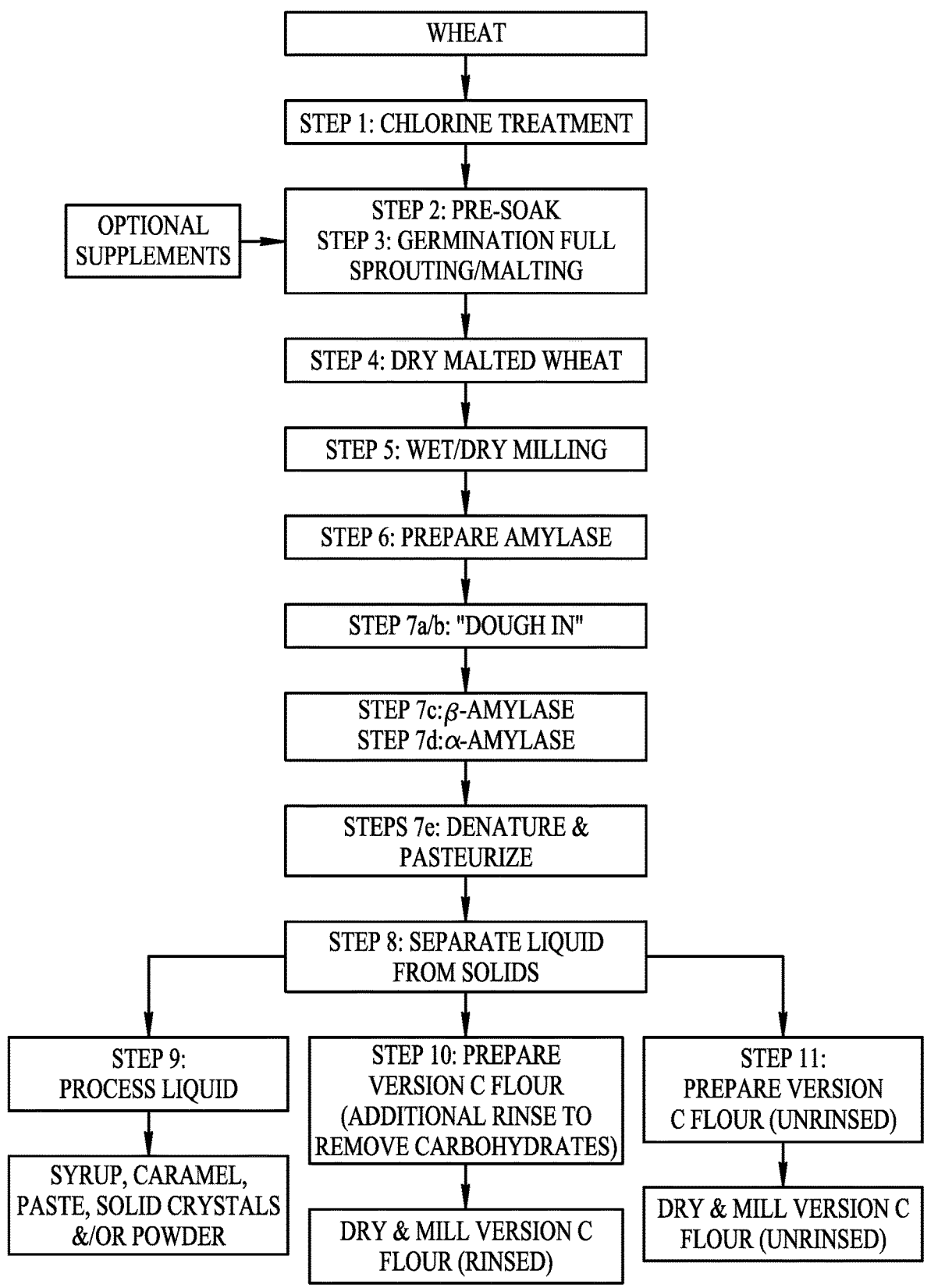
FIG. 5 illustrates a process diagram as applied to malted grains or malted barley as a substrate.

As discussed above with respect to FIG. 4, the amylase preparation (Step 6 in FIG. 5) can occur at any time prior to the introduction of the amylase in Step 7 of FIG. 5.
Process 3 (See FIG. 6)
Inventive Flour Process Using Rice (White, Jasmine & Brown)

The inventive flour process can also be applied to rice, such as White, Jasmine, and Brown Rice. This process can be applied (with substrate-specific variations) to any variety of rice including glutinous and non-glutinous varieties, thereby producing unique and hereto undiscovered flour and liquid products.

Figure 6:
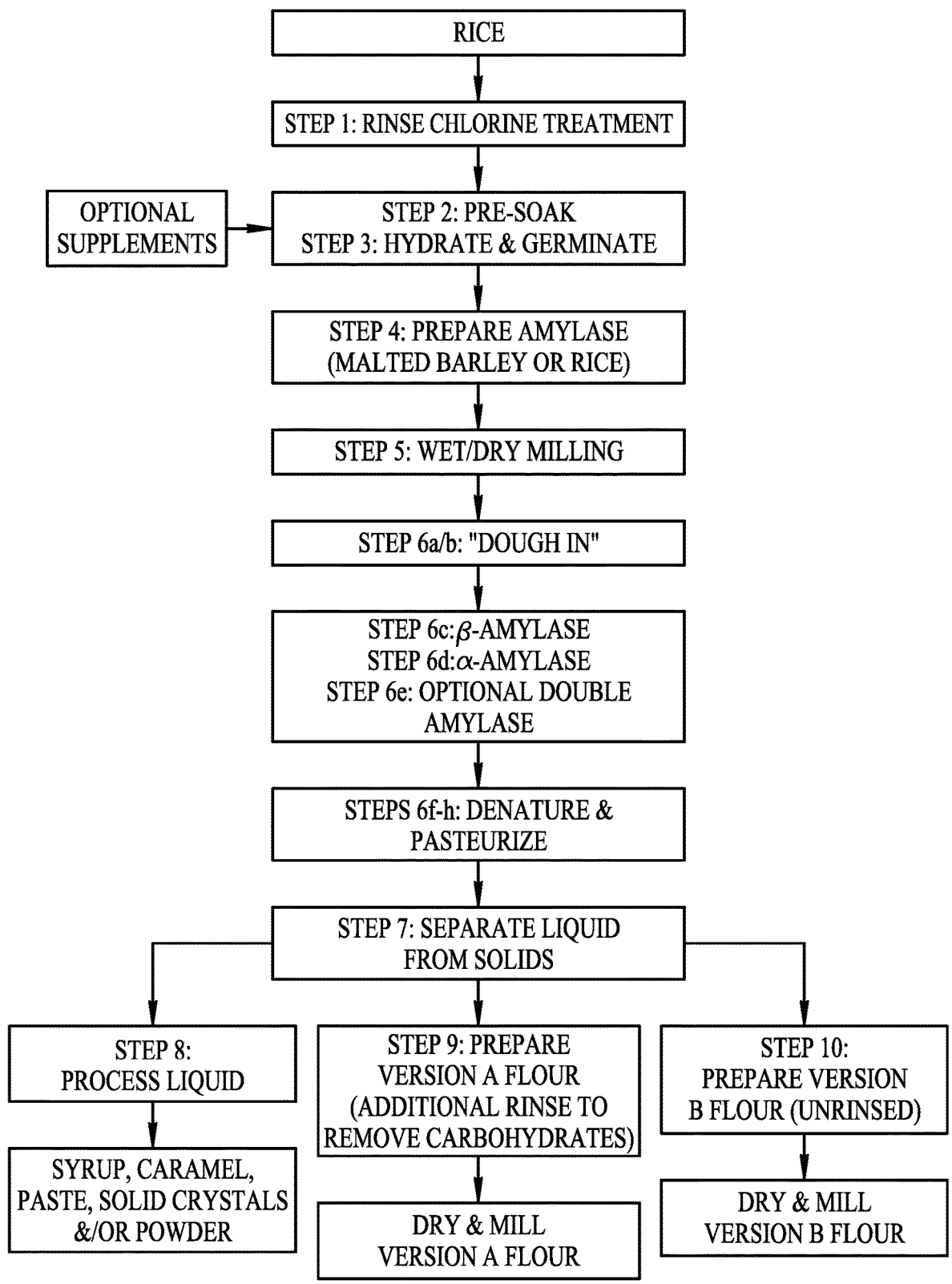
FIG. 6 illustrates a process diagram as applied to rice as a substrate.

The process for making rice inventive flour and inventive sweetened liquid is the same as that described for Process 1, Version A with rice as the substrate instead of wheat, as shown in the process diagram of FIG. 6. Although Version A is produced in the exemplary embodiment described herein, the process for making Version B of the inventive flour with rice is the same as that described for Process 1, Version B with rice as the substrate instead of wheat, as shown in the process diagram of FIG. 6.

A few noteworthy comments include:
  a. The previous processes described the use of malted barley as the amylase source. In the present process, it is possible to utilize malted barley, malted rice, or other products as the amylase source. If malted rice is used, the percentage of malted rice will likely be around 20% as measured on a dry volume basis, i.e., before the hydration begins. Those skilled in the art will appreciate that the time and temperature of the activated β-amylase and α-amylase can be optimized through testing. If malted rice is to be used for the amylase, then a similar procedure for fully sprouting, malting, drying and milling the malted rice into a flour to be blended with the other substrates as a non-barley option can be used. Those skilled in the art will appreciate that the specific time, temperature, and process can be varied to optimize the end-products and characteristics. It may be that a higher percentage of the rice amylase will have to be used as the blend—possibly 20% by dry ratios. Variation in the process can improve the enzymatic conversion and optimum amylase production for several varieties of rice to select the best one for a particular end product and application. It is also probable that there are variations depending on the particular strain for rice. It may be practical to use a blend of malted barley to assist in the saccharification process.
  b. Fracturing, tearing or shearing the germinated grain (Step 5). After cleansing, hydration and germination is complete, the rice hull must then be fractured or sheared in order to expose the inner-grain to the native and added β- and α-amylase during the cooking process. The process must mechanically cut the germinated grain. Hydrated and germinated rice each have their unique qualities per variety. For example, the white rice had a dramatically different consistency than the brown rice. The best ways to prepare each of the hydrated and germinated rice grains can be readily determined by those skilled in the art. The key is to expose the kernel without completely pulverizing the grain. It is likely a dry-milled process similar to cracking the germinated wheat will provide distinct advantages. However, those skilled in the art will appreciate that Step 5 can be implemented using wet milling or dry milling as discussed above in Process 1, Steps 5a and 5b, respectively.

Figure 7:
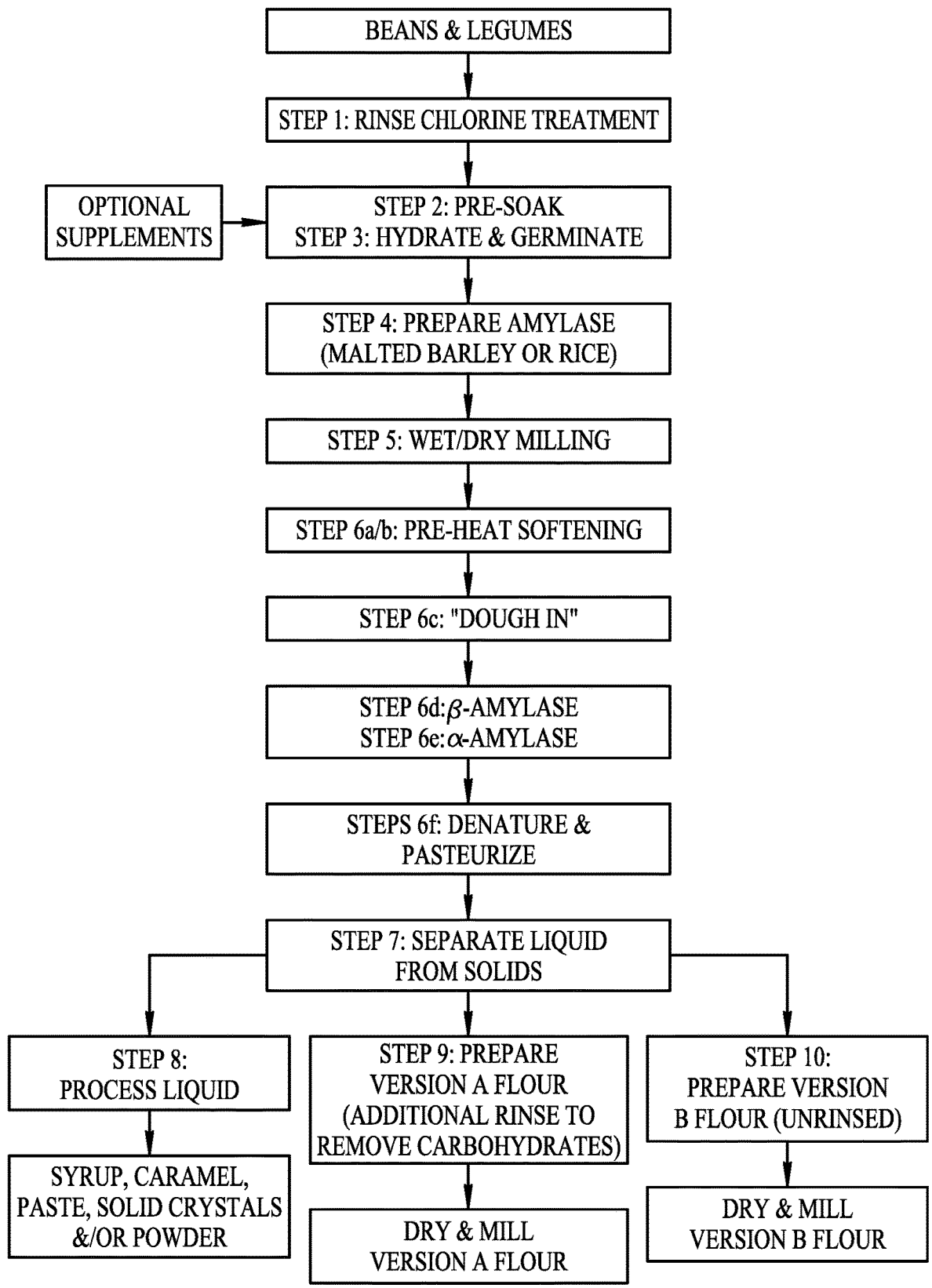
FIG. 7 illustrates a process diagram as applied to beans or legumes as a substrate.

As discussed above with respect to FIG. 4, the amylase preparation (Step 4 in FIG. 6) can occur at any time prior to the introduction of the amylase in Step 6 of FIG. 6.
Process 4 (See FIG. 7)
Inventive Flour Process Using Legumes (Lentils) & Beans (Great Northern Beans FIG. 7 illustrates the inventive flour process to demonstrate that legumes can be used as substrate. The inventive flour process can be applied to non-wheat substrates in order to demonstrate the validity and applicability of this process multiple grains, legumes, and root vegetables. In this process, the inventive flour process was applied to beans (Great Northern White Beans) and legumes (Lentils). This process can be applied (with substrate-specific variations) to any variety of beans and legumes, thereby producing unique and hereto undiscovered products—both flour and liquid.

Steps 1 and 2 are the same as Process 1, Version A and Version B.

Step 3 is the same as Process 1 except the Great Northern Beans require approximately 24 hours after the initial 12 hour soaking and the lentils took about 16 hours after the initial 12 hour soaking to initiate germination. As previously noted, warmer temperatures will hasten the germination process.

Step 4—Malted Barley was used as the amylase source in this process. It may be possible to use malted rice or other products as the amylase source. If malted rice is used, it will require about 20% (measured as dry weight) ratio of the substrates.

As discussed above with respect to FIG. 4, the amylase preparation (Step 4 in FIG. 7) can occur at any time prior to the introduction of the amylase in Step 6 of FIG. 7.

Steps 5 and 6 differ substantially from Process 1, Version A and Version B.
Step 5—Fracturing, Tearing or Shearing the Germinated Beans and Lentils
  a. After cleansing, hydration and germination is complete, the bean and lentil hull must then be fractured or sheared in order to expose the inner-legume to the native and added β- and α-amylase during the cooking process. The process must mechanically cut the germinated legume. Hydrated and germinated beans and legumes will vary widely with each having their unique qualities per variety. For example, the larger Great Northern White Beans have a different consistency than the Lentils. One skilled in the art appreciate that the optimal technique to prepare each of the hydrated and germinated beans and legumes can vary depending on the desired characteristics of the end-product. The key is to expose the kernel for optimal saccharification and enzymatic conversion. For the purpose of the proof of concept for Process 4, a food processor/grinder was used to chop the beans to a particle size similar to rice grains. A meat grinder using 7 mm die head could also be used to shear the legumes. Other variations can be demonstrated to achieve the optimal process for preparing legumes. Step 5 can be implemented using wet milling or dry milling.
Step 6—Cooking the Bean/Barley Mash or Bean/Rice Amylase Mash:
  a. The beans and lentils require longer dough-in, preparation and cooking times than rice or wheat in order to get the beans to soften sufficiently to allow for optimum starch to sugar conversion. The following process was the same for the beans as for the lentils—each processed separately in different batches.
- b. Heat the water to 145°-155° F. prior to adding the fractured hydrolyzed beans or lentils. The volume of water should be 0.75-1.5 quarts of water per 1 pound of dry legumes depending on the variety and desired thickness of the mash. In an exemplary embodiment, 155° F. was selected and a water to dry bean ratio of 1 quart of water per 1 dry pound of dry lentils and 1 pound of dry white beans. The objective is to have a mash with a consistency similar to a thin oatmeal cooked cereal.
- c. Dough-In phase: Heat the water to 155° F. then add the beans or lentils (in separate batches) and mix thoroughly. Introducing the cooler legumes will reduce the entire mash temperature to approximately 145° F. This stage can take 45-90 minutes maintaining a temperature of 145°-155° F. during this phase.
- d. This actual time for this stage can vary considerably depending on the size and nature of the beans or legumes. The goal is to soften the legumes and break them down to allow for a complete exposure of the starches within the water & mash. A finer grind for the bean or using the meat grinder to shear the legumes will help in this. Other variations of this proof of concept may be readily determined by those skilled in the art.
- e. At all stages of heating, it is critical to ensure that no scorching occurs to the mash. This may darken the color and ruin the aroma and flavor of the product.
- f. The β-Amylase phase, α-Amylase phase, and the Denaturing the Amylase & Pasteurizing phase (Process 1, Step 6) of the process is the same as Version A and Version B.

Step 7—Separation of Liquid (Inventive Sweetened Liquid) from Solids (Flour)

This process is the same as (Process 1, Step 7) Version A and Version B. In the exemplary embodiment disclosed herein, only non-rinsed bean and non-rinsed lentil solids were used to produce a white bean flour and a lentil flour. However, it is possible to make both a rinsed and non-rinsed version—similar to Version A and Version B of the wheat.

Step 8—Preparing the Liquid—Bean-Based & Lentil-Based Inventive Sweetened Liquid
This process is the same as Version A and Version B except to note that:
- a. The inventive sweetened liquid derived from the Great Northern White bean has a white milky syrup consistency, while the inventive sweetened liquid derived from the lentils had a darker green/brown milky syrup consistency. The White Bean inventive sweetened liquid has virtually no odor and the Lentil inventive sweetened liquid has a more pronounced aroma similar to a mild lentil soup.

Step 9—Preparing the Inventive Flour from Bean and Lentil
This process is the same as Version A and Version B with the following observations:
- a. Inventive flour from White Bean and Lentil are anticipated to be high in protein and fiber, with additional residual carbohydrates (maltose), and micro-nutrients. As noted above, neither the beans nor lentils were subjected to a final water rinse—similar to Version A (Wheat). Both types had a very mild but pleasant taste and aroma. The lentil solids were more pronounced than the white bean, which was virtually odor and taste-free. It is anticipated that the bean and lentil-based inventive flour will have a number of beneficial applications as a partial displacement for wheat flour. By using malted rice-based amylase, the potential for producing a complete protein and ultra-high nutrition flour is very good.

Process 5 (See FIG. 8)
Inventive Flour Process Using Root Vegetables: Carrots & Russet Burbank Potatoes The inventive flour process has also been applied to root vegetable/tuber substrates to demonstrate the validity and applicability of this process on these non-germinating foods (Carrots and Russet Burbank Potatoes). We conclude that this process can be applied (with substrate-specific variations) to any variety of root vegetable or tuber, thereby producing another unique and hereto undiscovered product—both solid and liquid.

Figure 8:
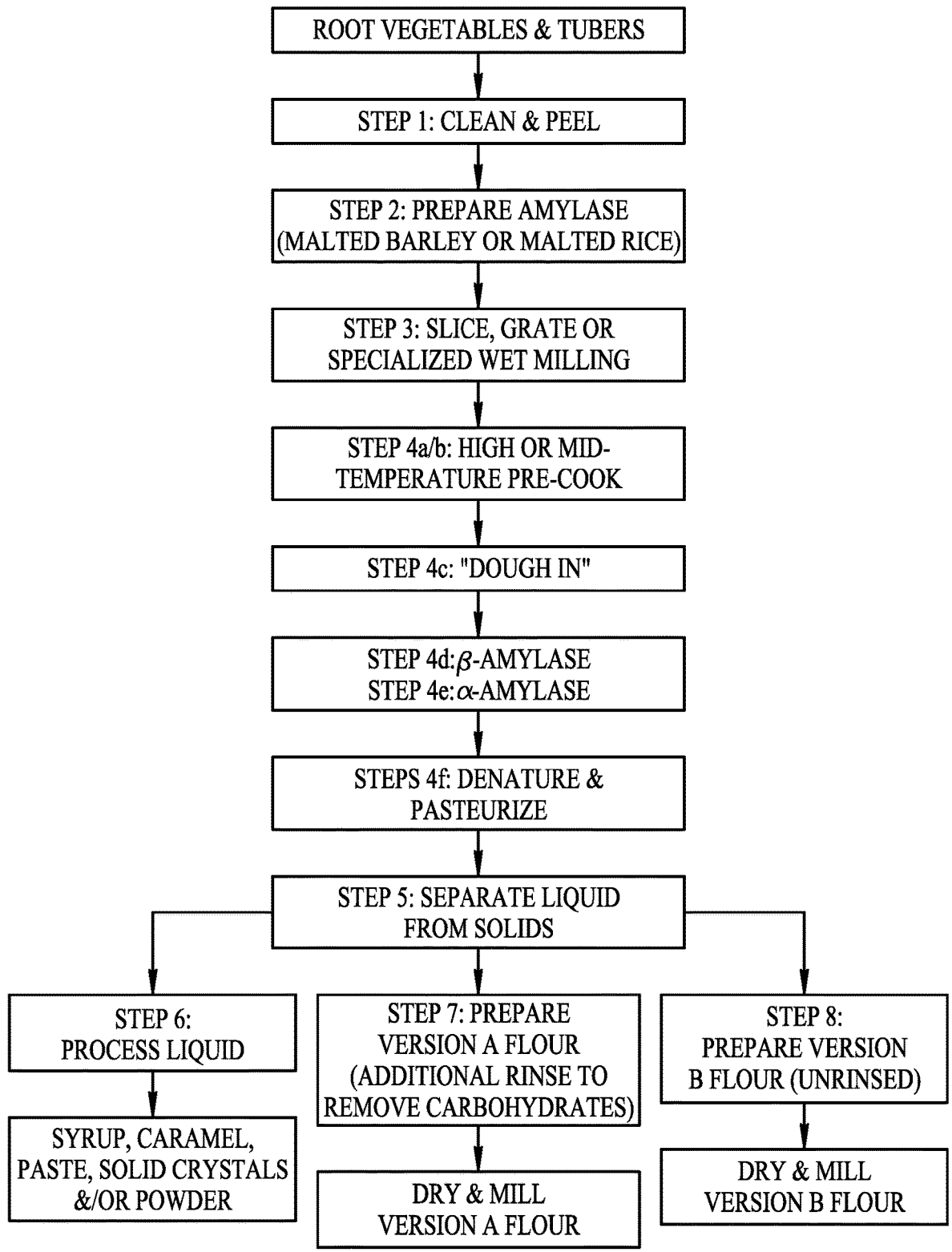
FIG. 8 illustrates a process diagram as applied to root vegetables or tubers as a substrate.

FIG. 8 illustrates a process applied in separate batches; one batch being carrots and the other batch being Russet Burbank Potatoes.

Step 1—Cleaning and Preparing the Carrots and Russet Potatoes
Step 1 is the same as Process 1 except for the following:
- a. Optional peeling of the substrate. In an exemplary embodiment, the carrots were not peeled, and the potatoes were peeled.
- b. Unlike grains, seeds, and legumes (e.g., Process 1, Step 2), there is no pre-soaking and germination phase when applying the inventive flour process to root vegetables and tubers.

Step 2—Preparing the Malted Barley (or Malted Rice) Amylase
- a. In an exemplary embodiment, malted barley was used as the amylase source although it is conceivable to use a non-wheat amylase, such as malted rice or other products.
- b. Utilize clean, No. 1 or highest premium malted barley from a reputable supplier. This must be brewer's grade malted barley.
- c. Mill the malted barley into the consistency of "bread-grade" flour. This will provide the β- and α-amylase for the saccharification process for starch to sugar conversion.
- d. The ideal ratio of malted barley is 8-10% barley to 92-90% root vegetables and tubers as measured on a dry volume basis, i.e., at the starting weight of the root vegetables and tubers—in this case carrots and potatoes. For example, if 10 pounds of potatoes are prepared, then add 1 lb. of milled, malted barley. Malted wheat or rice may be used as amylase sources as described previously. Those skilled in the art will appreciate that different quantities of amylase sources and conditions can be used to optimize the amylase hydrolysis of the starches.

As discussed above with respect to the previous processes, the amylase preparation (Step 2 in FIG. 8) can occur at any time prior to the introduction of the amylase in Step 4 of FIG. 8.

Step 3—Slicing or Grating the Carrots and Potatoes
- a. Clean the root vegetables and tubers, in this case carrots and potatoes, as described above.
- b. Whether or not the root vegetables or tubers are peeled depends on the specific type and variety.
- c. The carrots and potatoes are sliced very thin or grated to the consistency of hash browns. In an exemplary embodiment, both carrots and potatoes were sliced very thin using a food processor. The thickness was similar to kettle potato chips.

Step 4—Cooking the Carrots/Barley Amylase and Russet Potatoes/Barley Amylase Mash:

a. This initial cooking temperature will vary depending on the type and variety of root vegetable or tuber. This is based on the native amylase that may be present depending on the type of root vegetable or tuber used. For example, sweet potatoes contain a substantial amount of natural β-amylase which can be activated in the preparation of the tuber. As such, the preparation temperature of the water, prior to adding the amylase, will be lower (135°-145° F.) so as not to denature the native β-amylase. However, the tuber fibers will need to be broken down such that a much finer grind is necessary given the lower water temperature used in the "dough-in" or pre-amylase phase.

b. In an exemplary embodiment, no native amylase has been determined for carrots and potatoes, so a high temperature initial phase is used to break down the root fibers in preparation for the starch to sugar conversion. Heat the water to a simmer (200°-205° F.). The actual temperature will vary with elevation. The volume of water should be 0.5-0.75 quarts of water per 1 pound of root vegetables and tubers, depending on the variety and desired thickness of the mash. In an exemplary embodiment, simmering boil was selected and a water to substrate ratio of 0.5 quarts of water per 1 pound of carrots or 1 pound of potatoes was used. The objective is to have a thick mash similar to a thin oatmeal cooked cereal.

c. Dough-In phase: Heat the water to a low simmer of approximately 200°-205° F. then add the sliced potatoes or sliced carrots (in separate batches) and mix thoroughly. Continue a low simmer for approximately 10-30 minutes or until the root vegetables soften but are not completely mush.

d. This actual time for this stage can vary considerably depending on how the root vegetables or tubers are prepared, i.e., the size and thickness of the pieces as well as the variety. For example, the carrots took twice as long at this phase to soften as did the potatoes. As this process is applied to root vegetables is a proof of concept, there will be additional refinements.

e. Once the desired consistency is achieved, cease any heating, and let the water and substrate cool to 134°-140° F. in preparation for the introduction of the amylase. Since the cool-down phase can take some time, the softened substrate will continue to break down as the water cools.

f. At all stages of heating it is critical to ensure that no scorching occurs to the mash. This may darken the color and ruin the aroma and flavor of the product.

g. The β-Amylase phase, α-Amylase phase, Denaturing the Amylase & Pasteurizing phase and the Separation of Liquid (inventive sweetened liquid) from the Solid (flour) are the same as previously described for Version A and Version B.

Step 5—Separation of Liquid from Solids

Step 5 is the same as previously described in Process 1, Step 7.

Step 6—Preparing the Liquid

Step 6 is the same as previously described in Process 1, Step 8. In this proof of concept study, the inventive sweetened liquid derived from the russet potato substrate has a cloudy, milky syrup consistency, while the inventive sweetened liquid derived from carrot substrate has a darker rust color and is a syrup-like consistency. The Potato-based inventive sweetened liquid is slightly sweet with a pleasant aroma. The Carrot-based inventive sweetened liquid has a pleasant, sweet carrot aroma similar to sweet, cooked carrots.

Step 7—Preparing the Inventive Flour from Carrot and Potato a. inventive flour from Carrot and Potato are anticipated to be high in fiber and protein, with additional residual carbohydrates (maltose) and micro-nutrients. In the exemplary embodiment disclosed herein, neither the carrot nor potato mash were subjected to a final water rinse—similar to Version B wheat-based flour. Both varieties of flour are anticipated to be reduced in carbohydrates/calories, with elevated protein and fiber. Both types had a very mild but pleasant taste and aroma. The carrot flour was more pronounced with a sweet carrot flavor.

In summary, a unique process is described to reduce carbohydrate in grains (wheat and rice), legumes (beans and lentils) and root vegetables/tubers (carrot and potatoes) that results in a relative increase in protein, fiber and other nutrients in the solid phase. The liquid phase is high in carbohydrate, soluble fiber, and protein. The resulting solid phase is used to make baking flour while the liquid phase is turned into the inventive sweetened liquid or other products (e.g., sweetener) after dehydration.

Although the processes described herein describes the use of natural amylase sources, such as malted barley, malted rice, and the like, any of the processes described above may be implemented using a synthetic amylase in place of the natural sources. Indeed, those skilled in the art will appreciate that a glycolytic enzyme could be used as the source of enzymes to covert starch to their constituent sugars in any of the processes described above.

The foregoing described embodiments depict different components contained within, or connected with, different other components. It is to be understood that such depicted processes and end products are merely exemplary, and that in fact many other substrates, processes, and end-products can be implemented which achieve the same functionality. In a conceptual sense, any arrangement of steps to achieve the same functionality is effectively "associated" such that the desired functionality is achieved. Hence, any two processes herein combined to achieve a particular functionality can be seen as "associated with" each other such that the desired functionality is achieved, irrespective of starting substrates or intermediate components.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

REFERENCES

1. Medical News Today: 35/96 (36%) of the most read (popular) health news stories for 2017 were related to nutrition and diet.
2. Anderson J W, et al. Health benefits of dietary fiber. Nutrition Reviews. 2009; 67:188.
3. Dietary, functional and total fiber. Institute of Medicine. http://www.nap.edu/openbook.php?record_id=10490&page=339. Accessed Aug. 30, 2015.
4. Colditz G A. Healthy diet in adults. http://www.uptodate.com/home. Accessed Aug. 30, 2015.
5. Position of the American Dietetic Association: Health implications of dietary fiber. Journal of the American Dietetic Association. 2008; 108:1716.
6. Whole grains and fiber. American Heart Association. http://www.heart.org/HEARTORG/GettingHealthy/NutritionCenter/HealthyDietGoals/Whole-Grains-and-Fiber_UCM_303249_Article.jsp. Accessed Aug. 30, 2015.
7. Duyff R L. Carbs: Sugar, starches, fiber. In: American Dietetic Association Complete Food and Nutrition Guide. 4th ed. Hoboken, N.J.: John Wiley & Sons; 2012.
8. Rasco, B. A., Downey, S. E. and Dong, F. M. 1987. Consumer acceptability of baked goods containing distillers' dried grains with solubles from soft white winter wheat. *Cereal Chemistry.* 64:139-143.
9. San Buenaventura, M. L., Dong, F. M. and Rasco, B. A. 1987. The total dietary fiber content of distillers' dried grains with solubles. *Cereal Chemistry.* 64:135.
10. Rasco, B. A., Hashisaka, A. E., Dong, F. M. and Einstein, M. A. 1989. Sensory evaluation of baked goods incorporating different levels of distillers' dried grains with solubles from white wheat. *J. Food Science.* 54(2):337-342.
11. Rasco, B. A., Gazzaz, S. S. and Dong, F. M. 1990. Iron, calcium, zinc and phytic acid content of yeast-raised breads containing distillers' dried grains and other fiber ingredients. *J. Food Composition and Analysis.* 3:88-95.
12. Rasco, B. A., Rubenthaler, G., Borhan, M. and Dong, F. M. 1990. Baking properties of breads and cookies incorporating distillers' or brewer's grains from wheat or barley. *J. Food Science.* 55(2):424-429.
13. Maga, J. A., and K. E. van Everen. 1989. Chemical and sensory properties of whole wheat pasta products supplemented with wheat-derived dried distillers grain (DDG). Journal of Food Processing & Preservation. 13(1): 71-78.
14. Rasco; Barbara A., McBurney; William J. Human food product produced from dried distillers' spent cereal grains and solubles USPTO U.S. Pat. No. 4,828,846 May 9, 1989.

The invention claimed is:

1. A process for enhancing protein and fiber content of a starch-containing substrate comprising:
    incubating the starch-containing substrate containing grain, seed, legume or bean kernels having protein and fiber in water suspension at a first temperature for a first period of time to promote an initial phase of germination;
    following the first period of time, flushing the water used in the water suspension and maintaining hydration of the starch-containing substrate at a second temperature for a second period of time to germinate the grain, seed, legume or bean kernels to provide a partially germinated substrate that has acrospires having an average length no longer than ¼ to ⅓ the length of the grain, seed, legume or bean kernels;
    following the second period of time, milling the partially germinated substrate to fracture the grain, seed, legume or bean kernels so as to release the starch for saccharification;
    heating a mixture of water and the milled partially germinated substrate at a third temperature for a third period of time to initiate β-amylase initial saccharification of the starch in the mixture;
    following the third period of time, heating the mixture to a fourth temperature for a fourth period of time, the fourth temperature being greater than the third temperature, to thereby initiate further α-amylase saccharification of the starch in the mixture;
    following the fourth period of time, heating the mixture to a fifth temperature for a fifth period of time, the fifth temperature being greater than the fourth temperature, to thereby denature β-amylase and α-amylase enzymes and terminate any further saccharification of the starch in the mixture;
    separating the mixture into a liquid portion and a solid portion; and
    drying the solid portion to reduce the water content to thereby produce a dried product with enhanced protein and fiber content that can be used for the preparation of foods for human consumption.

2. The process of claim 1, further comprising:
    prior to drying the solid portion, rinsing the solid portion to remove additional residual sugar; and
    milling the rinsed and dried product with enhanced protein and fiber content into a flour.

3. The process of claim 1, further comprising filtering the liquid portion to remove any particulate material and thereby form a sweetened liquid.

4. The process of claim 3 wherein the sweetened liquid is used as an ingredient in a product selected from a list of products consisting of energy drinks, smoothies, nutrition bars, and protein bars.

5. The process of claim 3, further comprising removing a portion of the water in the sweetened liquid to provide a concentrated sweetener.

6. The process of claim 3, further comprising removing a sufficient portion of the water in the sweetened liquid to produce a crystalline form from the liquid portion.

7. The process of claim 1, further comprising:
prior to milling, drying the partially germinated substrate to suspend any further germination and place the partially germinated substrate in a dormant condition; and
the milling comprising dry-milling of the dried partially germinated substrate.

8. The process of claim 7, further comprising:
prior to the third period of time, re-hydrating the dry-milled partially germinated substrate by heating a mixture of water and the dry-milled partially germinated substrate at a sixth temperature for a sixth period of time to prepare the mixture for saccharification, the mixture of water and the dry-milled partially germinated substrate being the mixture used during the third period of time.

9. The process of claim 1, wherein the foods for human consumption comprise a cereal product.

10. The process of claim 1, wherein the starch-containing substrate is wheat, barley, oats, spelt, rye, or rice.

11. The process of claim 1, further comprising:
during the third period of time, incrementally adding amylase enzymes to the mixture.

12. The process of claim 11 wherein the added amylase enzymes are provided by a germinated or malted grain.

13. The process of claim 11, wherein the added amylase enzymes are provided by a malted barley or a malted rice.

14. The process of claim 11 wherein the starch-containing substrate is one or more grains selected from a group of grains consisting of wheat, barley, rye, oats, buckwheat, rice, wild rice, couscous, corn, sorghum, amaranth, tritcale, flax, teff, millet, kasha, quinoa, and kernza.

15. The process of claim 11 wherein the starch-containing substrate is one or more legumes selected from a group of legumes consisting of beans, lentils, peas, peanuts, and lupins.

16. The process of claim 1 wherein the process comprising one or more of the following:
a) the first period of time extends from 10 to 14 hours;
b) the second period of time extends from 12 to 24 hours;
c) the first temperature ranges from 55-70° F.; or
d) the second temperature does not exceed 74° F.

17. The process of claim 1 wherein the fifth period of time extends from 5 to 10 minutes and the fifth temperature ranges from 198-200° F.

* * * * *